(12) United States Patent
Dunman et al.

(10) Patent No.: US 10,028,931 B2
(45) Date of Patent: Jul. 24, 2018

(54) SYNERGISTIC COMPOSITIONS FOR TREATING MICROBIAL INFECTIONS

(71) Applicants: UNIVERSITY OF ROCHESTER, Rochester, NY (US); TEMPLE UNIVERSITY—OF THE COMMONWEALTH SYSTEM OF HIGHER EDUCATION, Philadelphia, PA (US)

(72) Inventors: Paul M. Dunman, Pittsford, NY (US); Wayne Childers, New Hope, PA (US)

(73) Assignees: University of Rochester, Rochester, NY (US); Temple University—Of the Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 15/521,623

(22) PCT Filed: Oct. 30, 2015

(86) PCT No.: PCT/US2015/058278
§ 371 (c)(1),
(2) Date: Apr. 25, 2017

(87) PCT Pub. No.: WO2016/070021
PCT Pub. Date: May 6, 2016

(65) Prior Publication Data
US 2017/0246139 A1    Aug. 31, 2017

Related U.S. Application Data

(60) Provisional application No. 62/073,100, filed on Oct. 31, 2014.

(51) Int. Cl.
*A61K 31/341* (2006.01)
*A61K 31/443* (2006.01)
(Continued)

(52) U.S. Cl.
CPC .......... *A61K 31/341* (2013.01); *A61K 9/0043* (2013.01); *A61K 9/06* (2013.01);
(Continued)

(58) Field of Classification Search
None
See application file for complete search history.

(56) References Cited

U.S. PATENT DOCUMENTS

2003/0134904 A1    7/2003    Giordano et al.
2009/0215764 A1    8/2009    Das et al.
(Continued)

FOREIGN PATENT DOCUMENTS

WO    2012054738 A1    4/2012

OTHER PUBLICATIONS

"The Ribonuclease RnpA is a Novel Target for Antimicrobial Development" Tess Marie Eidem, Dissertation, University of Nebraska Medical Center, Omaha, Nebraska, Dec. 2013.*
(Continued)

*Primary Examiner* — Karl J Puttlitz
(74) *Attorney, Agent, or Firm* — Kilpatrick Townsend & Stockton LLP

(57) ABSTRACT

Synergistic pharmaceutical compositions including an RNase P inhibitor and a tRNA synthetase inhibitor are provided, as well as methods for their use in treating infections. Also provided herein are methods of using the compositions to inhibit a bacterial tRNA synthetase in a cell and to decolonize bacteria on a surface.

10 Claims, 2 Drawing Sheets

(51) Int. Cl.

| | |
|---|---|
| *A61K 31/17* | (2006.01) |
| *A61K 31/381* | (2006.01) |
| *A61K 31/497* | (2006.01) |
| *A61K 31/343* | (2006.01) |
| *A61K 31/415* | (2006.01) |
| *A61K 31/4409* | (2006.01) |
| *A61K 31/4045* | (2006.01) |
| *A61K 31/4184* | (2006.01) |
| *A61K 31/47* | (2006.01) |
| *A61K 31/44* | (2006.01) |
| *A61K 45/06* | (2006.01) |
| *A61K 31/351* | (2006.01) |
| *A61K 47/10* | (2017.01) |
| *A61K 9/06* | (2006.01) |
| *A61K 9/00* | (2006.01) |

(52) U.S. Cl.
CPC ............ *A61K 31/17* (2013.01); *A61K 31/343* (2013.01); *A61K 31/351* (2013.01); *A61K 31/381* (2013.01); *A61K 31/4045* (2013.01); *A61K 31/415* (2013.01); *A61K 31/4184* (2013.01); *A61K 31/44* (2013.01); *A61K 31/443* (2013.01); *A61K 31/4409* (2013.01); *A61K 31/47* (2013.01); *A61K 31/497* (2013.01); *A61K 45/06* (2013.01); *A61K 47/10* (2013.01)

(56) References Cited

U.S. PATENT DOCUMENTS

| | | |
|---|---|---|
| 2011/0151490 A1 | 6/2011 | Hillman et al. |
| 2011/0207726 A1 | 8/2011 | Diamond et al. |
| 2013/0281360 A1 | 10/2013 | Romesberg et al. |
| 2013/0296386 A1 | 11/2013 | Dunman et al. |

OTHER PUBLICATIONS

Collier et al.,"Reducing the pill burden" CMAJ Feb. 7, 2012 vol. 184 No. 2 First published Jan. 9, 2012.*

Hurdle et al., "Prospects for aminoacyl-tRNA synthetase inhibitors as new antimicrobial agents", 2005, Antimicrobial Agents and Chemotherapy, 49(12):4821-4833.

Lv et al., "Aminoacyl-tRNA synthetase inhibitors as potent antibacterials", 2012, Current Medicinal Chemistry 19:3550-3563.

Ochsner et al., "Mode of action and biochemical characterization of REP8839, a novel inhibitor of methionyl-tRNA synthetase" ,2005, Antimicrobial Agents and Chemotherapy, 49(10):4253-4262.

Orelle et al., "Identifying the targets of aminoacyl-tRNA synthetase inhibitors by primer extension inhibition", 2013, Nucleic Acids Research 1-9.

PCT/US2015/058278, "International Preliminary Report on Patentability", dated May 11, 2017, 8 pages.

PCT/US2015/058278, "International Search Report and Written Opinion", dated Jan. 20, 2016, 11 pages.

Teng et al., "Identification of bacteria selective threonyl tRNA synthetase (ThrRS) substrate inhibitors by structure-based design", 2013, J. Med. Chem. 56:1748-1760.

Zhao, et al., "In silico discovery of aminoacyl-tRNA synthetase inhibitors", 2014, Int. J. Mol. Sci, 15:1358-1373.

Abad et al., "Does the Nose Know? An Update on MRSA Decolonization Strategies", Current Infectious Disease Reports, vol. 15, No. 6, Oct. 24, 2013, pp. 455-464.

Buurman et al., "Novel Rapidly Diversifiable Antimicrobial RNA Polymerase Switch Region Inhibitors with Confirmed Mode of Action in Haemophilus influenzae", Journal of Bacteriology, vol. 194, No. 20, 2012, pp. 5504-5512.

EP15854238.1, "Extended European Search Report", dated Apr. 18, 2018, 4 pages.

* cited by examiner

SYNERGISTIC COMPOSITIONS FOR TREATING MICROBIAL INFECTIONS

CROSS REFERENCE TO PRIORITY APPLICATION

This application claims priority to U.S. Provisional Application No. 62/073,100, filed Oct. 31, 2014, which is incorporated herein by reference in its entirety.

STATEMENT REGARDING FEDERALLY FUNDED RESEARCH

This invention was made with government support under grant numbers AI103507 and AI073780, awarded by the National Institutes of Health. The government has certain rights in the invention.

BACKGROUND

Methicillin-resistant *Staphylococcus aureus* (MRSA) is a predominant cause of hospital-acquired infections, which were recently classified as "preventable medical errors" that are not covered by certain federal health insurance programs. In response, healthcare facilities have enacted MRSA infection control measures to reduce incidences of hospital-acquired infections. For example, healthcare facilities administer mupirocin-based ointments to incoming patients harboring *S. aureus* as a means of reducing MRSA transmission and disease. However, mupirocin-resistant (intermediate resistant and complete resistant) MRSA strains have emerged that are recalcitrant to mupirocin-treatment practices.

SUMMARY

Described herein are synergistic pharmaceutical compositions including an RNase P inhibitor and a tRNA synthetase inhibitor. Also described herein are methods of using the synergistic compositions for treating microbial infections, inhibiting a bacterial tRNA synthetase in a cell, and decolonizing bacteria on a surface.

A pharmaceutical composition described herein includes an RNase P inhibitor of the following formula:

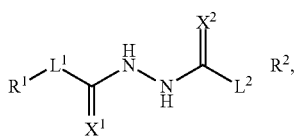

or a pharmaceutically acceptable salt or prodrug thereof, wherein $L^1$ and $L^2$ are each independently a direct bond or a divalent moiety selected from the group consisting of -substituted or unsubstituted alkyl-, -substituted or unsubstituted heteroalkyl-, -substituted or unsubstituted alkenyl-, -substituted or unsubstituted amino-, -substituted or unsubstituted amido-, and -substituted or unsubstituted alkoxy-; $R^1$ and $R^2$ are each independently selected from the group consisting of substituted or unsubstituted alkyl, substituted or unsubstituted alkenyl, substituted or unsubstituted cycloalkyl, substituted or unsubstituted aryl, and substituted or unsubstituted heteroaryl; and $X^1$ and $X^2$ are each independently O or S; and a tRNA synthetase inhibitor. Optionally, $X^1$ is O. Optionally, $X^2$ is S. The tRNA synthetase inhibitor is optionally mupirocin. The RNase P inhibitor is optionally a compound of the following formula:

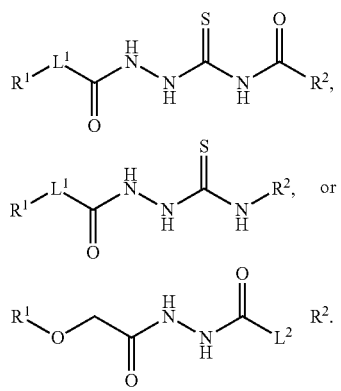

Optionally, the RNase P inhibitor is

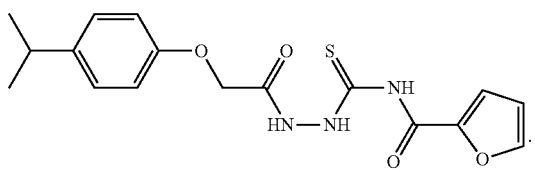 [SMILES: CC(C)c1ccc(OCC(=O)NNC(=S)NC(=O)c2ccco2)cc1]

A pharmaceutical composition described herein includes an RNase P inhibitor of the following formula:

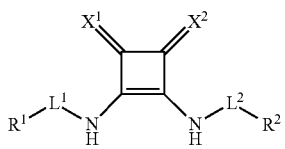

or a pharmaceutically acceptable salt or prodrug thereof, wherein $L^1$ and $L^2$ are each independently selected from the group consisting of substituted or unsubstituted alkyl or substituted or unsubstituted heteroalkyl; $R^1$ and $R^2$ are each independently selected from the group consisting of substituted or unsubstituted aryl or substituted or unsubstituted heteroaryl; and $X^1$ and $X^2$ are each independently O or S; and a tRNA synthetase inhibitor. Optionally, the tRNA synthetase inhibitor is mupirocin.

A pharmaceutical composition described herein includes an RNase P inhibitor of the following structure:

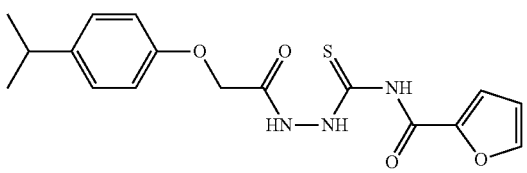 [SMILES: CC(C)c1ccc(OCC(=O)NNC(=S)NC(=O)c2ccco2)cc1]

and mupirocin.

Optionally, the compositions described herein further comprise a pharmaceutically acceptable carrier. Optionally, the carrier is a polyalkylene glycol carrier (e.g., a polyethylene glycol carrier). Optionally, the composition is formulated as an ointment.

Also described herein are methods for treating or preventing a microbial infection in a subject. A method of treating or preventing a microbial infection in a subject includes administering to the subject an effective amount of a composition as described herein. The RNase P inhibitor and the tRNA synthetase inhibitor can be administered concomitantly or sequentially (in either order).

Optionally, the microbial infection is a bacterial infection. The bacterial infection can optionally be a *Staphylococcus* infection, such as a *Staphylococcus aureus* infection. Optionally, the *Staphylococcus aureus* infection is a drug-resistant *Staphylococcus aureus* infection (e.g., a mupirocin-resistant *Staphylococcus aureus* infection). The bacterial infection can optionally be a *Streptococcus* infection, such as a *Streptococcus pyogenes* infection.

Further described herein are methods of inhibiting a bacterial tRNA synthetase in a cell. A method of inhibiting a bacterial tRNA synthetase in a cell includes contacting the cell with an effective amount of a composition as described herein. Optionally, the cell is a *Staphylococcus aureus* cell. Optionally, the cell is a mupirocin-resistant cell. The cell can optionally be a mupirocin-resistant *Staphylococcus aureus* cell. Optionally, the cell is a *Streptococcus pyogenes* cell.

Also described herein are methods of decolonizing bacteria on a surface. A method of decolonizing bacteria on a surface includes contacting the surface with an effective amount of a composition as described herein. Optionally, the surface is a human body surface, such as a mucosal surface (e.g., a nasal cavity surface).

The details of one or more embodiments are set forth in the drawings and the description below. Other features, objects, and advantages will be apparent from the description and drawings, and from the claims.

DETAILED DESCRIPTION

Figure 1:
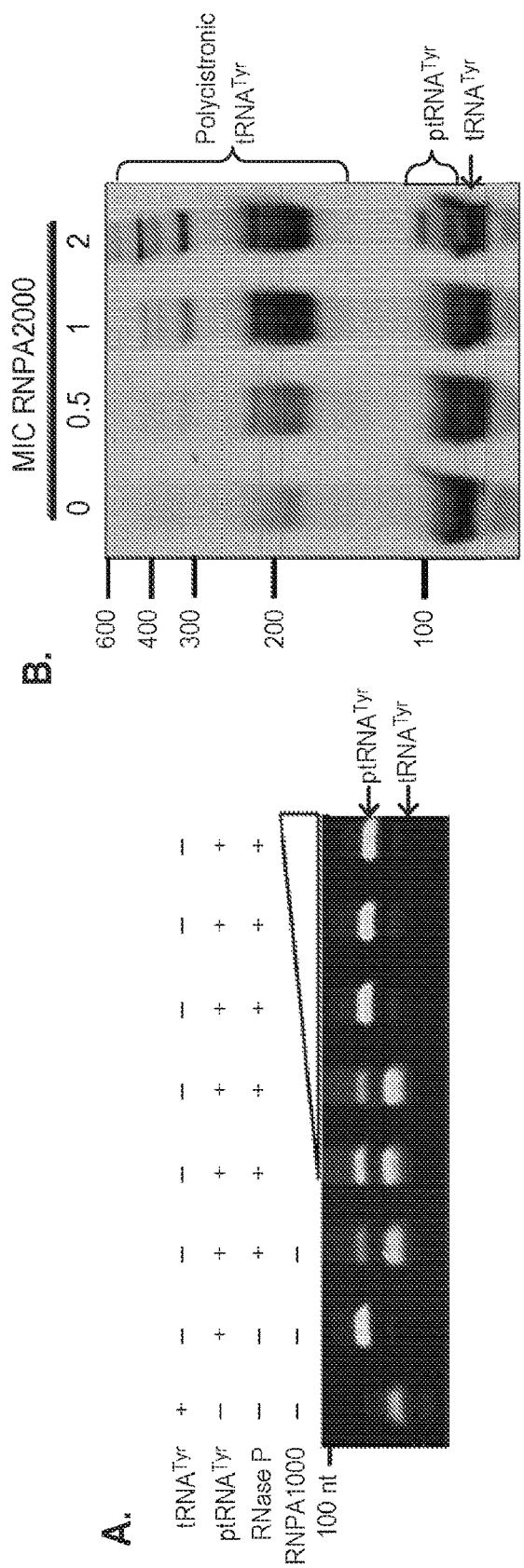
FIG. 1 contains photographs demonstrating that RNPA2000 inhibits RNase P-mediated tRNA processing in vitro (Panel A) and in bacterial cells (Panel B).

Described herein are synergistic pharmaceutical compositions including an RNase P inhibitor and a tRNA synthetase inhibitor. Optionally, the RNase P inhibitor is an RnpA inhibitor and/or an RnpB inhibitor. Optionally, the tRNA synthetase inhibitor is a microbial tRNA synthetase inhibitor. Also described herein are methods of using the synergistic compositions for treating microbial infections, inhibiting a bacterial tRNA synthetase in a cell, and decolonizing bacteria on a surface.

I. Compositions

The synergistic pharmaceutical compositions described herein include at least one RNase P inhibitor and at least one tRNA synthetase inhibitor.

a. RNase P Inhibitors

A class of RNase P inhibitors useful in the methods described herein comprises compounds represented by Formula I:

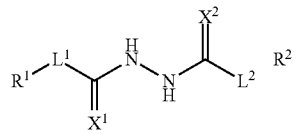

or a pharmaceutically acceptable salt or prodrug thereof.

In Formula I, $L^1$ and $L^2$ are each independently a direct bond or a divalent moiety selected from the group consisting of -substituted or unsubstituted alkyl-, -substituted or unsubstituted heteroalkyl-, -substituted or unsubstituted alkenyl-, -substituted or unsubstituted amino-, -substituted or unsubstituted amido-, and -substituted or unsubstituted alkoxy-.

Also in Formula I, $R^1$ and $R^2$ are each independently selected from the group consisting of substituted or unsubstituted alkyl, substituted or unsubstituted alkenyl, substituted or unsubstituted cycloalkyl, substituted or unsubstituted aryl, and substituted or unsubstituted heteroaryl.

Additionally in Formula I, $X^1$ and $X^2$ are each independently O or S. Optionally, $X^1$ is O. Optionally, $X^2$ is S.

As used herein, the term direct bond indicates a covalent bond. When $L^1$ is a direct bond, it is a covalent bond between $R^1$ or an atom of $R^1$ and the carbon of the (C=$X^1$) group. When $L^2$ is a direct bond, it is a covalent bond between $R^2$ or an atom of $R^2$ and the carbon of the (C=$X^2$) group.

As used herein, the terms alkyl and alkenyl include straight- and branched-chain monovalent substituents. Examples include methyl, ethyl, isobutyl, allyl, and the like. Ranges of these groups useful with the compounds and methods described herein include $C_1$-$C_{20}$ alkyl and $C_2$-$C_{20}$ alkenyl. Additional ranges of these groups useful with the compounds and methods described herein include $C_1$-$C_{12}$ alkyl, $C_2$-$C_{12}$ alkenyl, $C_1$-$C_6$ alkyl, $C_2$-$C_6$ alkenyl, $C_1$-$C_4$ alkyl, and $C_2$-$C_4$ alkenyl.

Heteroalkyl and heteroalkenyl are defined similarly as alkyl and alkenyl, but can contain O, S, or N heteroatoms or combinations thereof within the backbone. Ranges of these groups useful with the compounds and methods described herein include $C_1$-$C_{20}$ heteroalkyl and $C_2$-$C_{20}$ heteroalkenyl. Additional ranges of these groups useful with the compounds and methods described herein include $C_1$-$C_{12}$ heteroalkyl, $C_2$-$C_{12}$ heteroalkenyl, $C_1$-$C_6$ heteroalkyl, $C_2$-$C_6$ heteroalkenyl, $C_1$-$C_4$ heteroalkyl, and $C_2$-$C_4$ heteroalkenyl.

The terms cycloalkyl and cycloalkenyl include cyclic alkyl groups having a single cyclic ring or multiple condensed rings. Examples include cyclohexyl, cyclopentylethyl, and adamantanyl. Ranges of these groups useful with the compounds and methods described herein include $C_3$-$C_{20}$ cycloalkyl and $C_3$-$C_{20}$ cycloalkenyl. Additional ranges of these groups useful with the compounds and methods described herein include $C_5$-$C_{12}$ cycloalkyl, $C_5$-$C_{12}$ cycloalkenyl, $C_5$-$C_6$ cycloalkyl, and $C_5$-$C_6$ cycloalkenyl.

Aryl molecules include, for example, cyclic hydrocarbons that incorporate one or more planar sets of, typically, six carbon atoms that are connected by delocalized electrons numbering the same as if they consisted of alternating single and double covalent bonds. An example of an aryl molecule is benzene. Heteroaryl molecules include substitutions along their main cyclic chain of atoms such as O, N, or S. When heteroatoms are introduced, a set of five atoms, e.g., four carbon and a heteroatom, can create an aromatic system. Examples of heteroaryl molecules include furan, pyrrole, thiophene, imadazole, oxazole, pyridine, and pyrazine. Aryl and heteroaryl molecules can also include additional fused rings, for example, benzofuran, indole, benzothiophene, naphthalene, anthracene, and quinoline. The aryl and heteroaryl molecules can be attached at any position on the ring, unless otherwise noted.

The alkyl, alkenyl, aryl, heteroalkyl, heteroalkenyl, heteroaryl, cycloalkyl, cycloalkenyl, aryl, or heteroaryl molecules used herein can be substituted or unsubstituted. As used herein, the term substituted includes the addition of an alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl group to a position attached to the main chain of the alkyl, alkenyl, aryl, heteroalkyl, heteroalkenyl, heteroaryl, cycloalkyl, cycloalkenyl, aryl, or heteroaryl, e.g., the replacement of a hydrogen by one of these molecules. Examples of substitution groups include, but are not limited to, hydroxyl, halogen (e.g., F, Br, Cl, or I), and carboxyl groups. Conversely, as used herein, the term unsubstituted indicates the alkyl, alkenyl, aryl, heteroalkyl, heteroalkenyl, heteroaryl, cycloalkyl, cycloalkenyl, aryl, or heteroaryl has a full complement of hydrogens, i.e., commensurate with its saturation level, with no substitutions, e.g., linear decane (—$(CH_2)_9$—$CH_3$).

In some examples of Formula I, $X^1$ is O, $X^2$ is S, and $L^2$ is —NHC(O)— to provide Structure I-A:

Structure I-A

In Structure I-A, $R^1$, $L^1$, and $R^2$ are as defined in Formula I.

In some examples of Formula I, $X^1$ is O, $X^2$ is S, and $L^2$ is —NH— to provide Structure I-B:

Structure I-B

In Structure I-B, $R^1$, $L^1$, and $R^2$ are as defined in Formula I.

In some examples of Formula I, $L^1$ is —$OCH_3$—, $X^1$ is O, and $X^2$ is O to provide Structure I-C:

Structure I-C

In Structure I-C, $L^1$, $X^1$, and $X^2$ are as defined in Formula I.

Examples of Formula I include the following compounds:

ST003531 (RNPA2000)

ST4145527

ST5254069

ST5254078

ST5254083

ST5254088

ST5254089

ST5521633

ST5521953

ST5522690
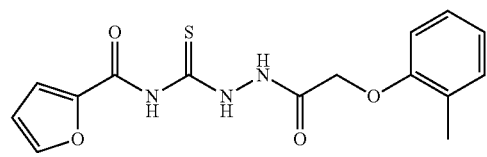
ST5522821
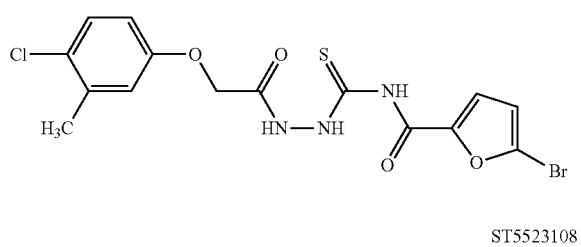
ST5523108
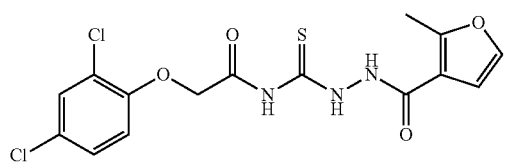
ST5523210
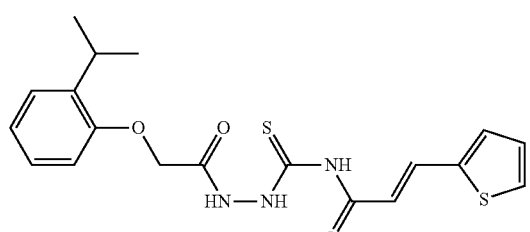
ST5523216
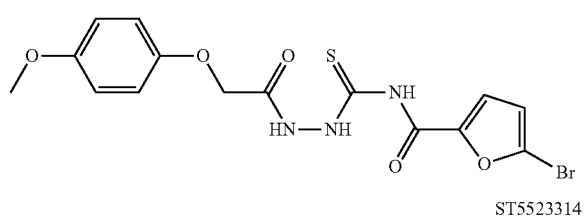
ST5523314
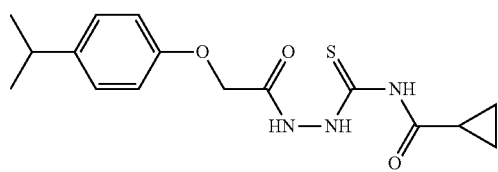
ST5523326
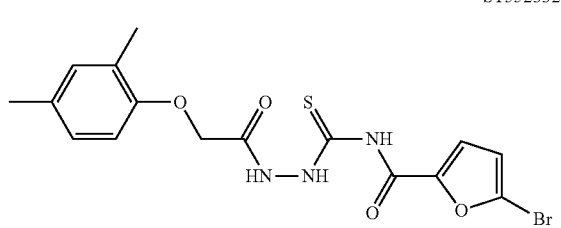
ST5523335
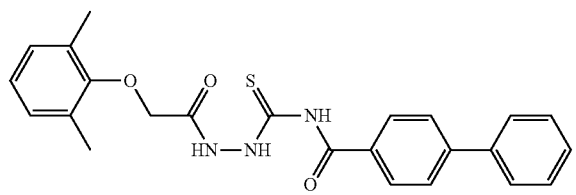
ST5523339
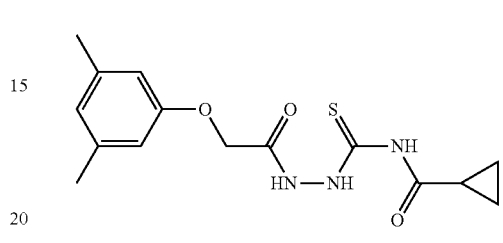
ST5524187
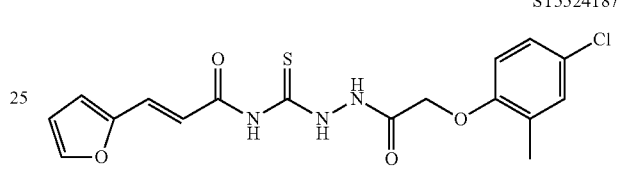
ST5524465
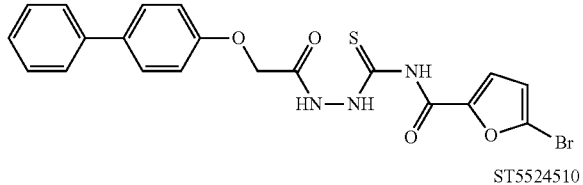
ST5524510
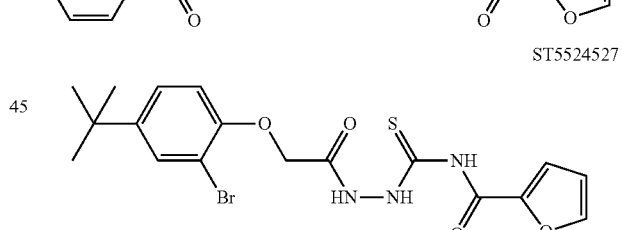
ST5524693
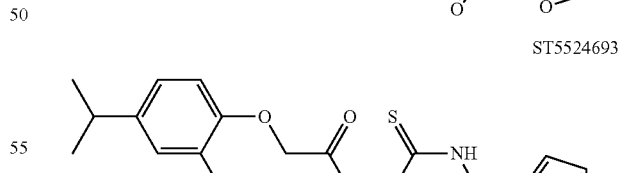
ST5524973
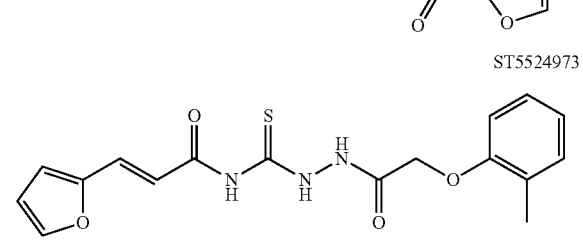

ST5524997
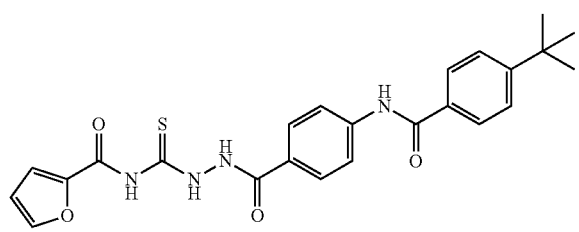
ST5525281
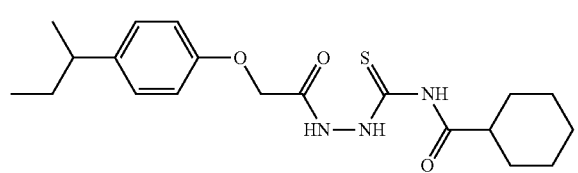
ST5525289
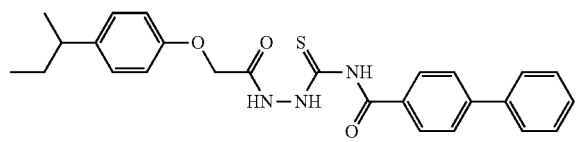
ST5525332
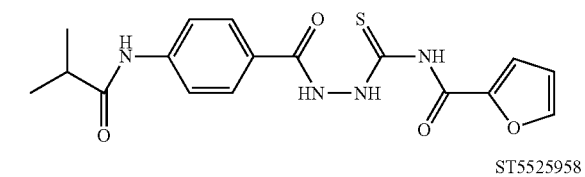
ST5525955
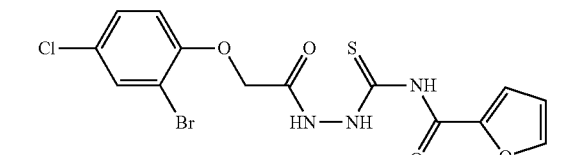
ST5525958
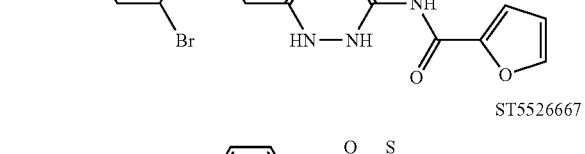
ST5526667
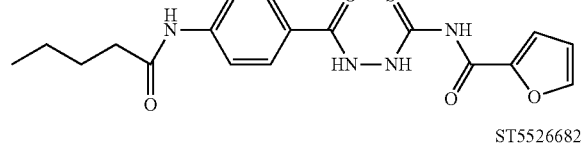
ST5526682
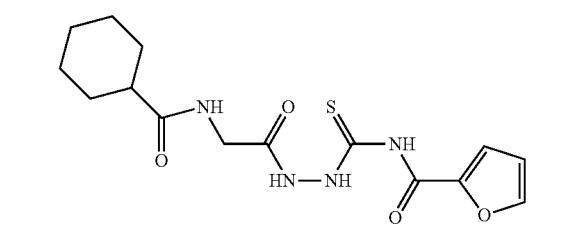
ST5528171
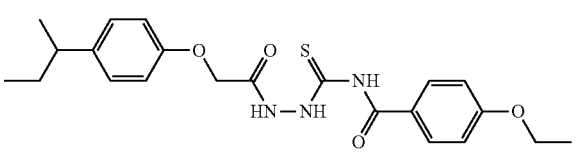
ST5528173
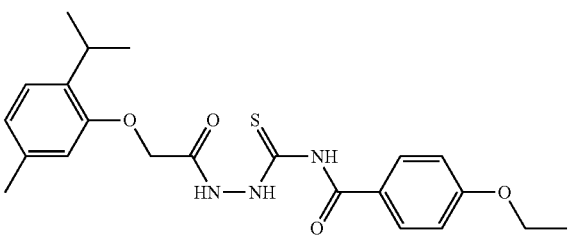
ST5528488
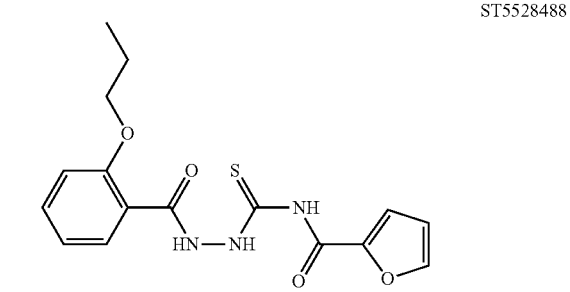
ST5528839
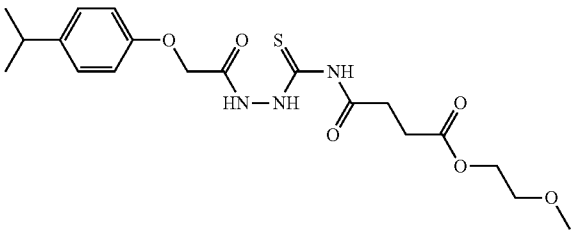
ST5528863
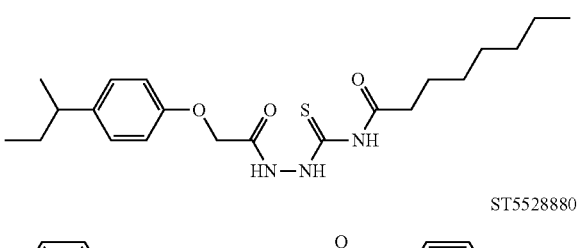
ST5528880
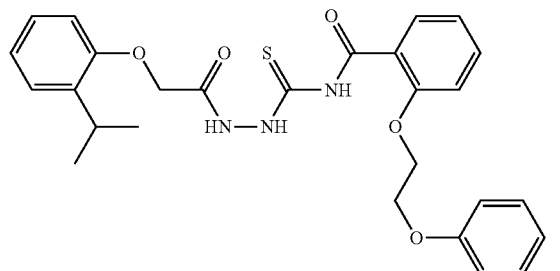

ST5528960
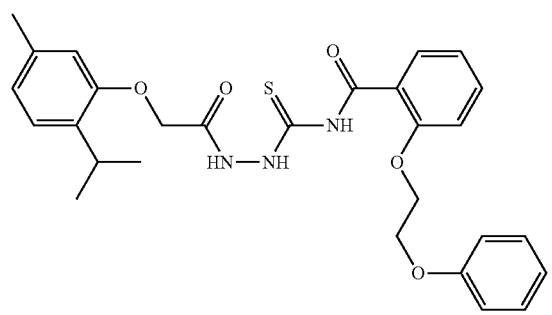
ST5607293
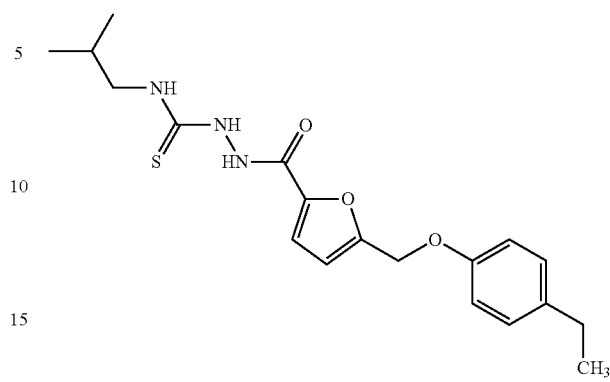
ST5529685
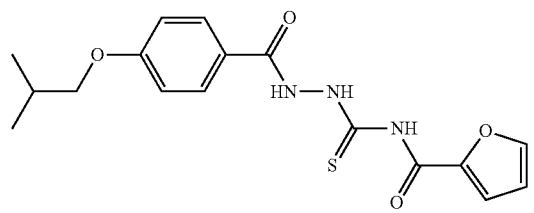
ST563647
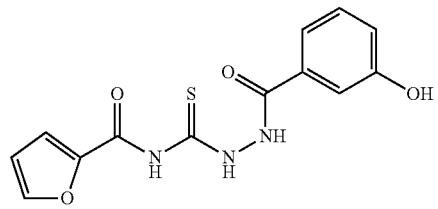
ST5607017
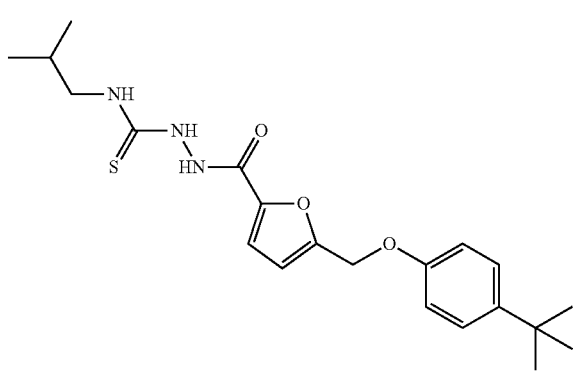
ST5638707
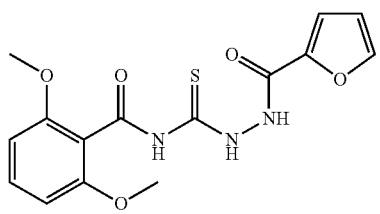
ST5638722
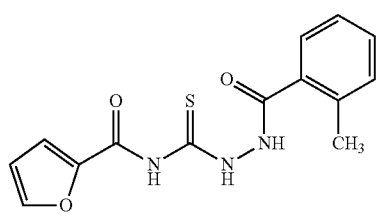
ST5640720
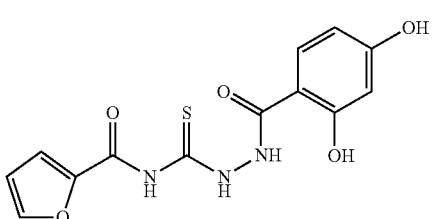
ST5607269
ST5641784
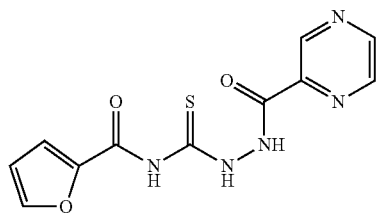

ST5642600
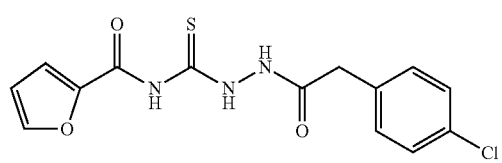
ST5682126
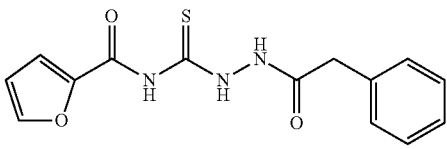
ST5682777
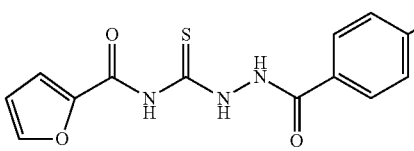
ST5682778
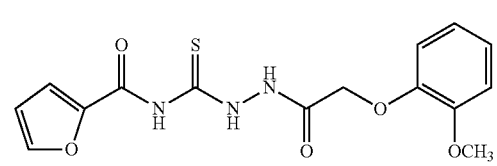
ST5682782
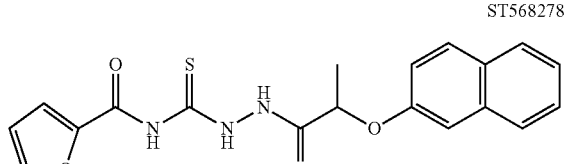
ST5682783
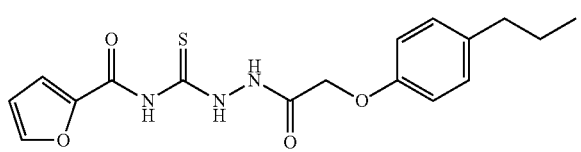
ST5682846
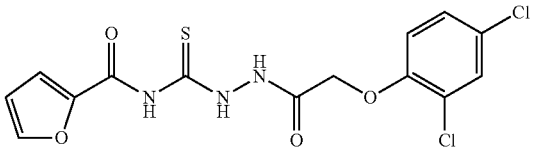
ST5684191
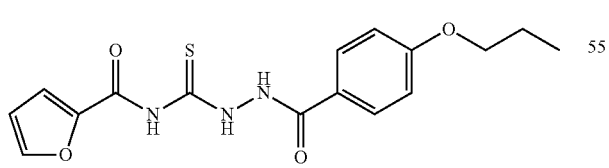
ST5703018
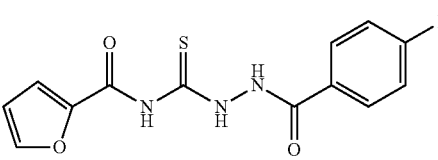
ST5703881
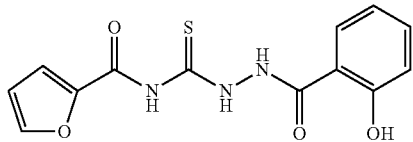
ST5704832
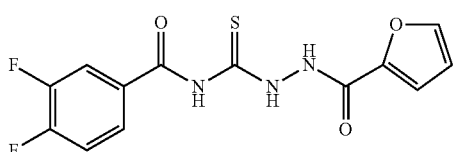
MC-190029
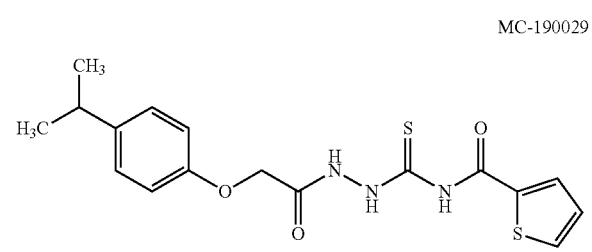
MC-190030
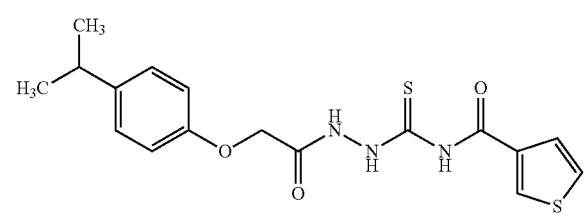
MC-190031
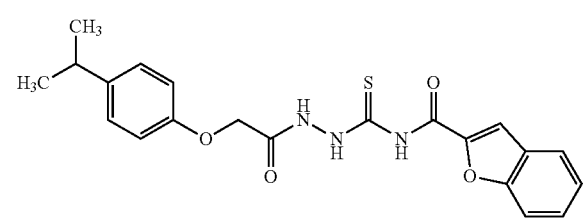
MC-190032
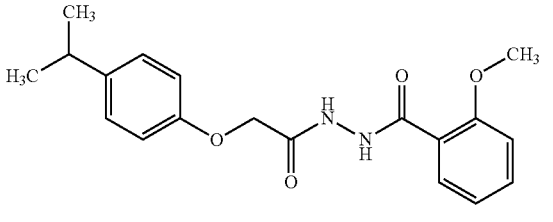
MC-190033
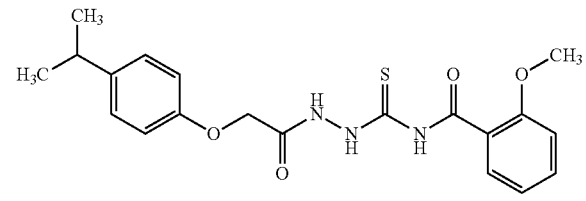

-continued
MC-190034
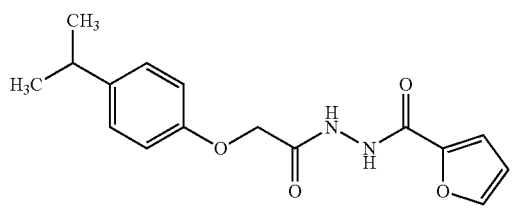
MC-190035
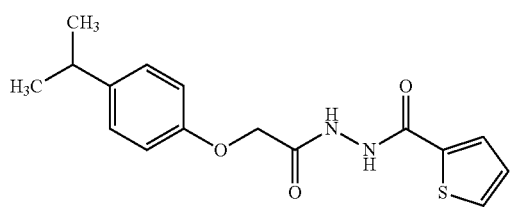
MC-190036
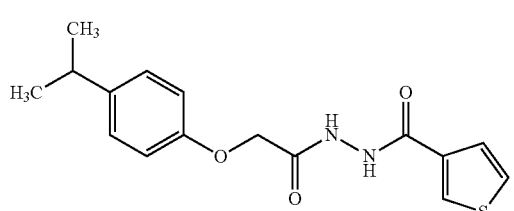
MC-190037
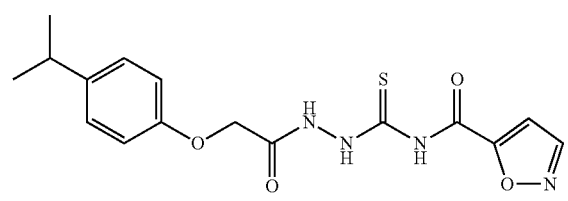
MC-190038
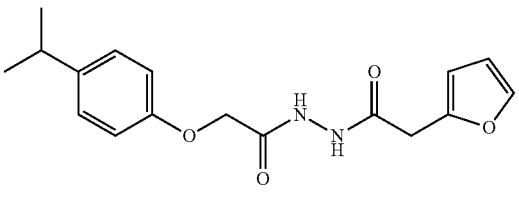
MC-220001
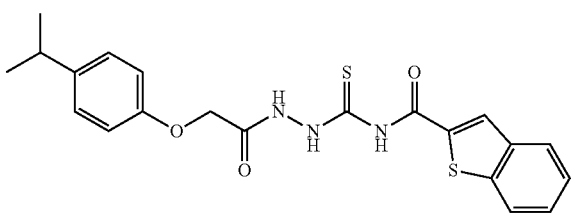
-continued
MC-190039
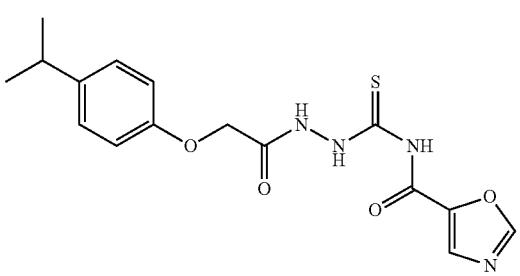
MC-190040
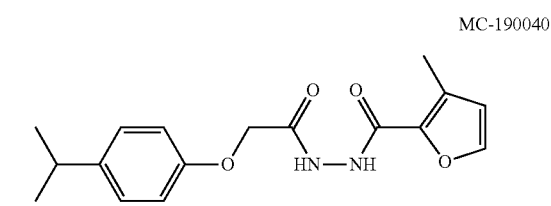
MC-190041
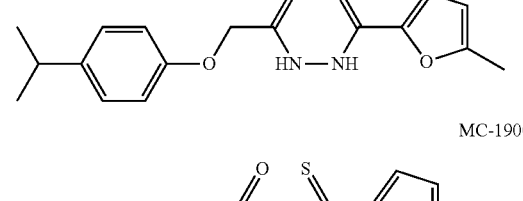
MC-190042
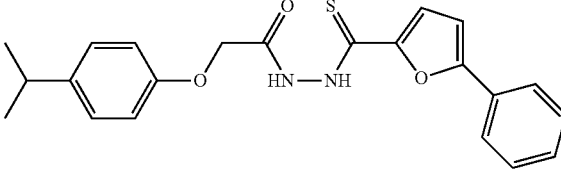
MC-190043
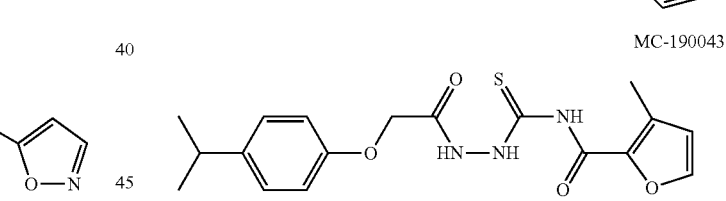
MC-190044
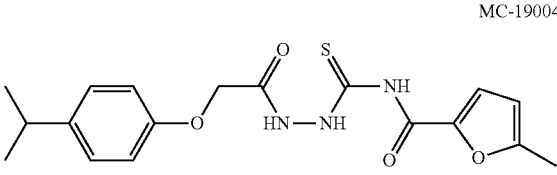
MC-190045
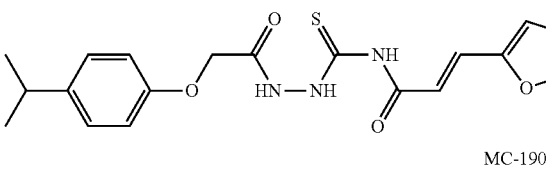
MC-190046
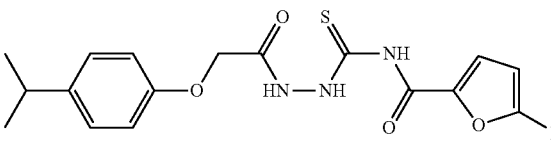

MC-190047
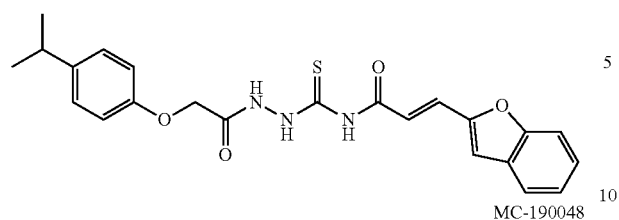
MC-190048
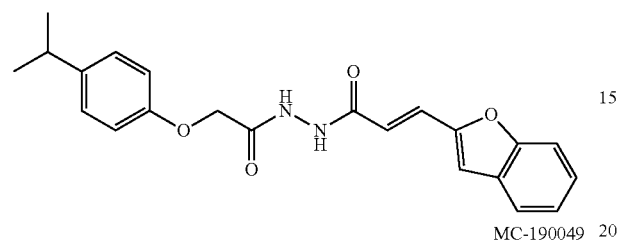
MC-190049
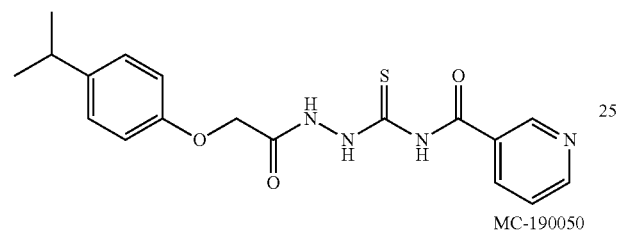
MC-190050
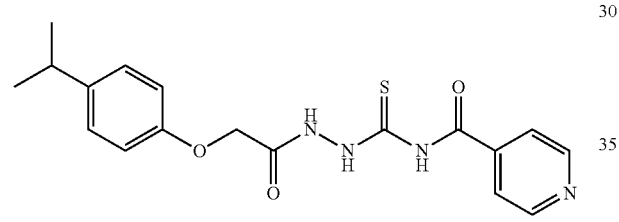
MC-190051
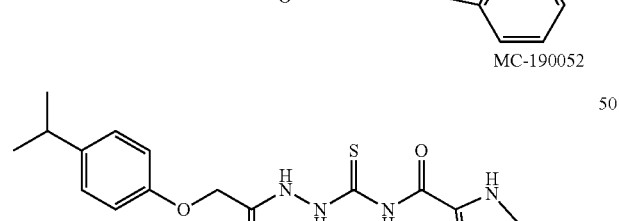
MC-190052
MC-190053
MC-190054
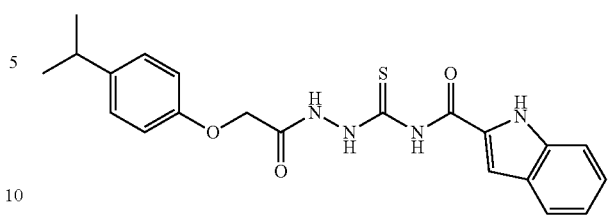
MC-190055
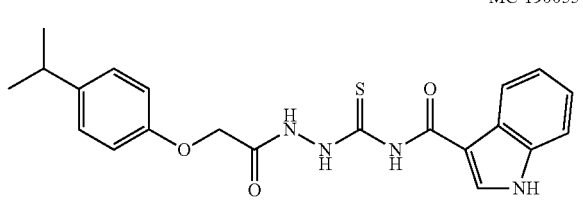
MC-190056
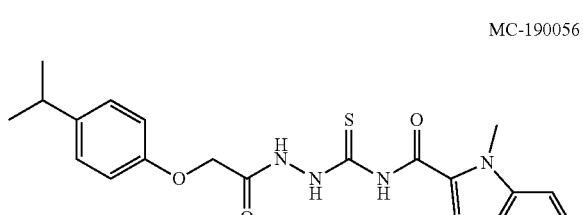
MC-190057
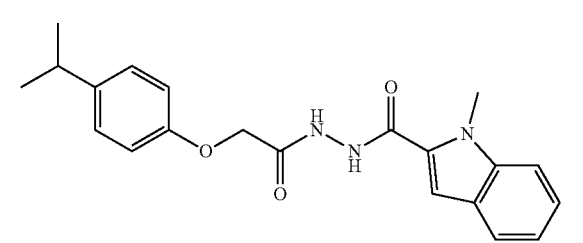
MC-190058
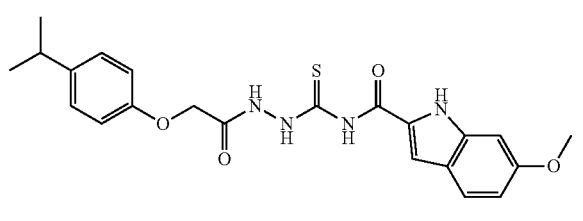
MC-190059
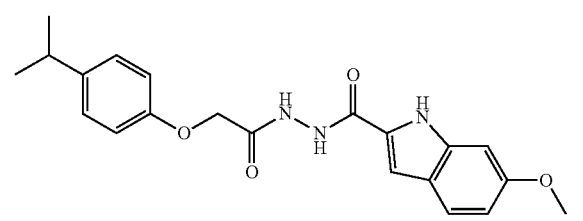

-continued
MC-190060
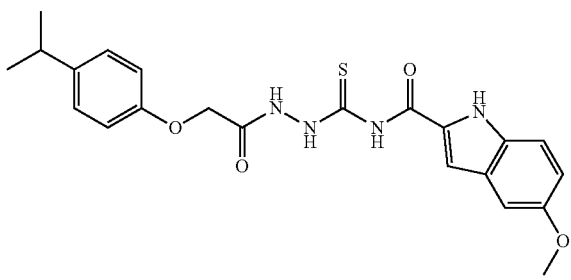
MC-190062
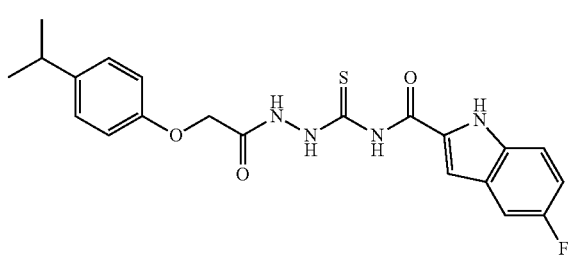
MC-190064
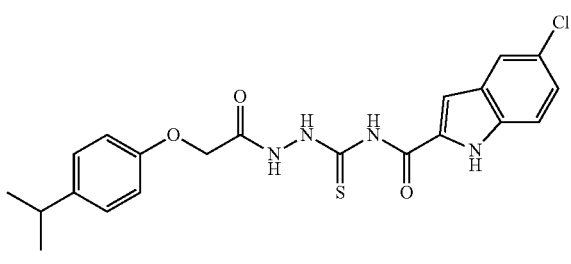
MC-190066
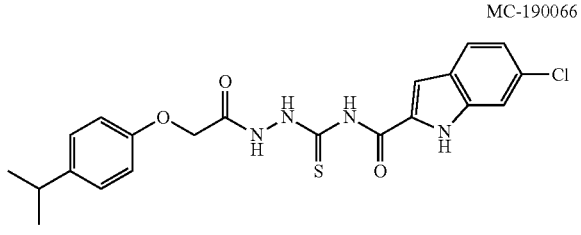
MC-190067
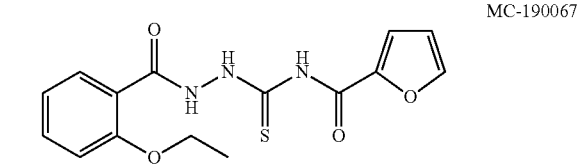
MC-190068
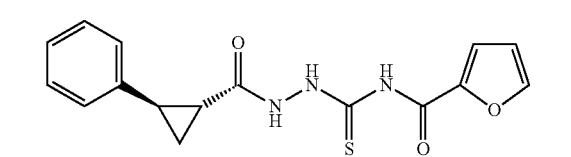
MC-190069
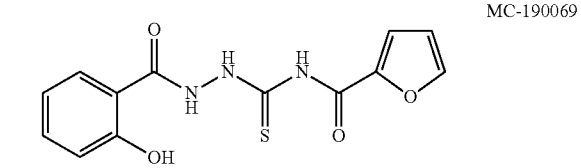
-continued
MC-190070
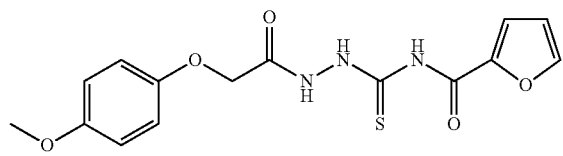
MC-190071
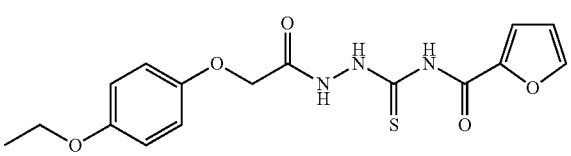
MC-190072
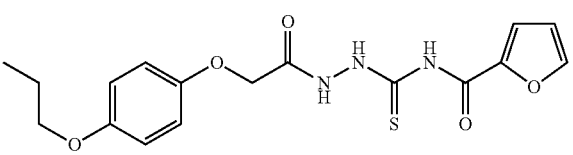
MC-190073
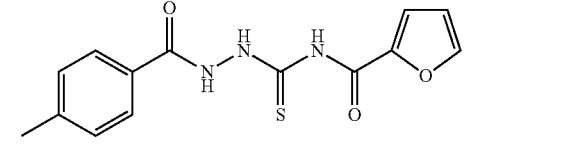
MC-190074
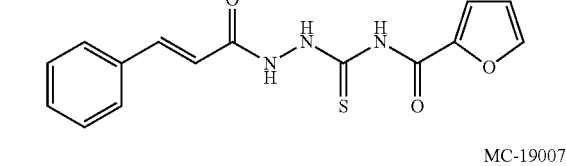
MC-190077
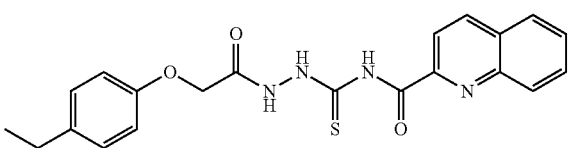
MC-190078
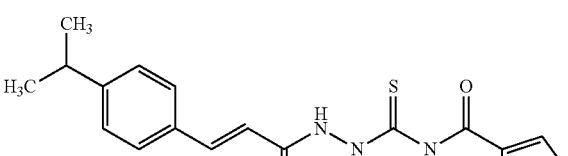
MC-190079
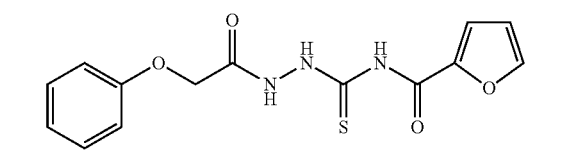

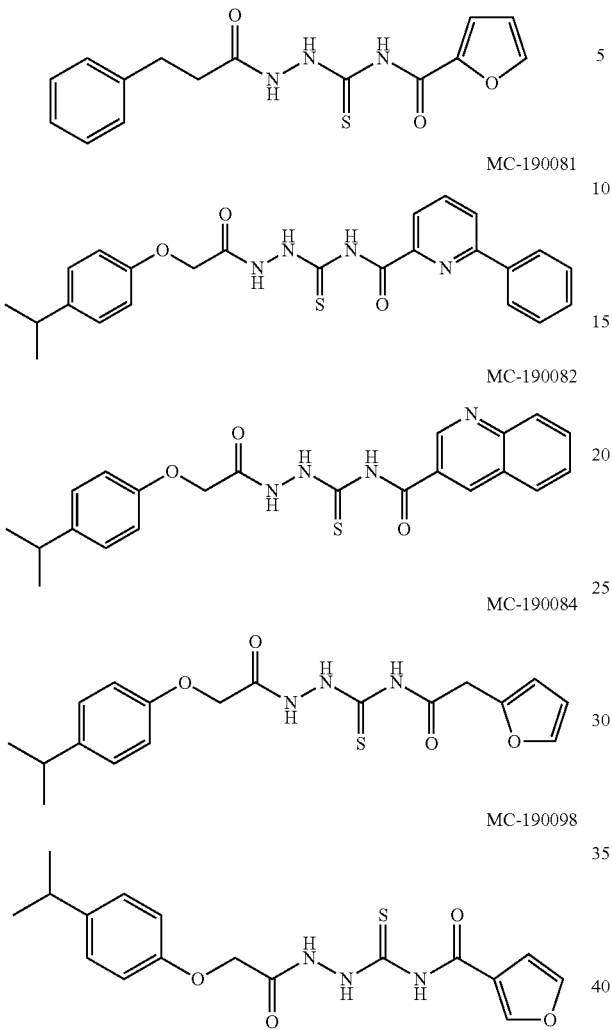

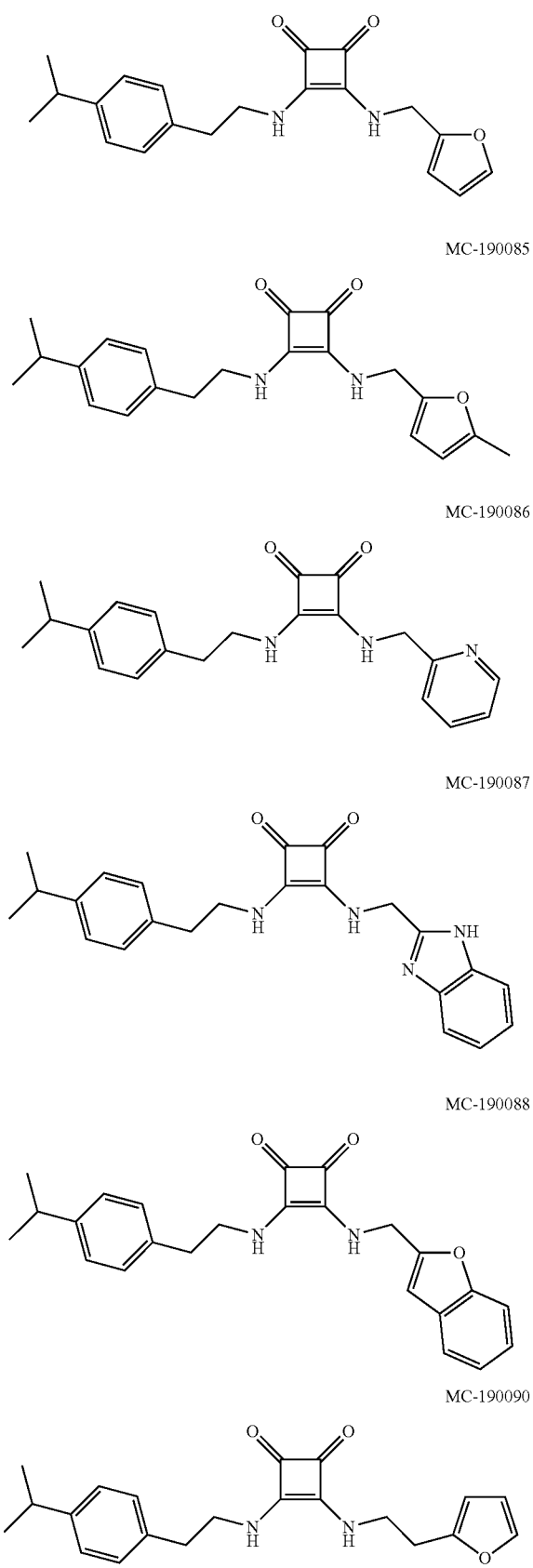

A class of RNase P inhibitors useful in the methods described herein comprises compounds represented by Formula II:

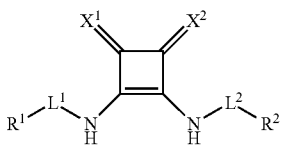

or a pharmaceutically acceptable salt or prodrug thereof.

In Formula II, $L^1$ and $L^2$ are each independently selected from the group consisting of substituted or unsubstituted alkyl or substituted or unsubstituted heteroalkyl.

Also in Formula II, $R^1$ and $R^2$ are each independently selected from the group consisting of substituted or unsubstituted aryl or substituted or unsubstituted heteroaryl.

Additionally in Formula II, $X^1$ and $X^2$ are each independently O or S.

Examples of Formula II include the following compounds:

MC-190091

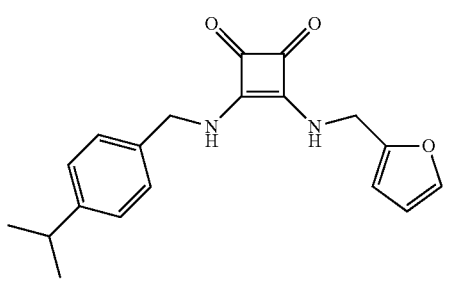

MC-190092

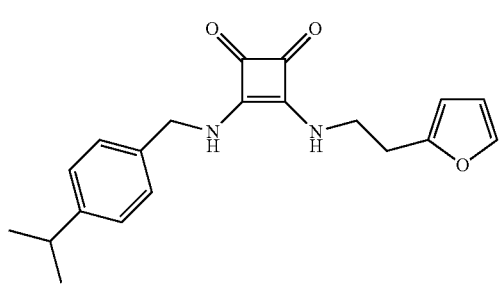

b. tRNA Synthetase Inhibitors

The synergistic combinations described herein further include one or more tRNA synthetase inhibitors. In some embodiments, the tRNA synthetase inhibitor is a microbial tRNA synthetase inhibitor. Optionally, the microbial tRNA synthetase inhibitor is a bacterial tRNA synthetase inhibitor.

The tRNA synthetase inhibitor can be an agent that inhibits a bacterial aminoacyl tRNA synthetase. Optionally, the bacterial aminoacyl tRNA synthetase can be a prolyl tRNA synthetase, a cysteinyl tRNA synthetase, a methionyl tRNA synthetase, a leucyl tRNA synthetase, a tryptophanyl tRNA synthetase, a glycyl tRNA synthetase, an alanyl tRNA synthetase, a valyl tRNA synthetase, an isoleucyl tRNA synthetase, an aspartyl tRNA synthetase, a glutamyl tRNA synthetase, an asparagyl tRNA synthetase, a glutaminyl tRNA synthetase, a seryl tRNA synthetase, a threonyl tRNA synthetase, a lysyl tRNA synthetase, an arginyl tRNA synthetase, a histidyl tRNA synthetase, a phenylalanyl tRNA synthetase, a tyrosyl tRNA synthetase, or a glutamyl-prolyl-tRNA synthetase (EPRS).

Optionally, the tRNA synthetase inhibitor can be a natural product inhibitor, an analog of a natural product inhibitor, or a pharmaceutically acceptable salt thereof. Optionally, the tRNA synthetase inhibitors can include mupirocin, borrelidin, furanomycin, granaticin, indolmycin, ochratoxin A, chuangxinmycin, and cis-pentacin. Optionally, the tRNA synthetase inhibitors can include S-trityl-L-cysteine; L-asparaginamide; 4-aza-DL-leucine; DL-serine hydroxamate; proflavine (hemisulfate salt); L-isoleucinol; N-phenylglycine; L-leucinol; L-methioninol; phe-leu-amide; tyramine; L-isoleucinol; 3,4-dehydro-DL-proline; S-carbamyl-L-cysteine; α-methyl-DL-methionine; chloro-L-alanine; cis-hydroxy proline; L-prolinol; L-histidonol; L-tyrprophan hydroxamate; DL-4-thiaisoleucine; DL-amino-ε-caprolactam; L-aspartic acid amide; DL-β-hydroxynorvaline; cis-4-fluoro-L-proline; trans-4-fluoro-L-carboxylic acid; α-methyl-DL-histidine; N-formyl-L-histidine; L-2-amino-3-sulfamoylpropionic acid; L-aspartic acid-β-hydroxamate; β-cyano-L-alanine; selenocystamine; 4-amino-n-butyric acid amide; DL-5-hydroxylysine; L-lysinhydroxamate; 3-(N-phenylacetyl)amino-2,6-piperidinedione (antineoplaston A10); 4-amino-4 phosphonobutyric acid; ethionamide; 1,2-diamino-3(4-imidazolyl) propane (histidinamine); α-methylhistidine; (S)-2-methylbutylamine; L-O-methyl-threonine; DL-armentomycin (2-amino-4,4-dichlorobutyric acid); DL-3-dehydroarmentomycin; DL-3-hydroxyleucine; 5,5,5-trifluoro-DL-leucine; β-(3-aminocyclohexyl)-DL-alanine; DL-p-chloroamphetamine; trans-2,6-diaminohex-4-enoic acid; DL-2,6-diphthalimidocaproic acid methyl ester; DL-5-hydroxylysine; L-lysinhydroxamate; DL-4-oxalysine; DL-4-selenalysine; L-methioninamide; 2-amino-4-methyl-hex-4-enoic acid; (1S,2S)-2-amino-1-phenyl-1,3-propanediol; N-benzyl-D-amphetamine; N-benzyl-L-phenylalanine; N-benzyl-D-phenylethylamine; 1,3-bis(acetoxy)-2-nitro-1-phenylpropane (fenitropan); 1,2-diamino-3-(2,6-dichlorophenyl)propane; 1,2-diamino-3-hydroxy-5-phenylpentane; 1,2-diamino-3-phenylpropane; N-(2,6-dichlorobenzylidene)-2-phenylethylamine; N-(2,6-dichlorobenzyl)-2-phenylethylamine; N-(4-fluorobenzyl)-L-phenylalanine; DL-2-fluorophenylalanine; 2-hydroxyethyl-2-phenylammonium sulfate; α- and β-methyl-DL-phenylalanine; L-phenylalaninol; L-α-phenylglycine; DL-threo-β-phenylserine; β-2-thienyl-DL-alanine; N-trifluroacetyl-L-phenylalanine cyclohexyl ester; 2-aminomethyl-4-isopropyloxypyrrolidine oxalate; 2-amino-methylpyrrolidine; L-4-thiaproline; N-benzylethanolamine; N-(2,6-dichlorobenzyl)ethanolamine; N-(2,6-dichlorobenzylidene)ethanolamine; DL-β-hydroxyleucine; 1,2-diamino-5-phenyl-3-pentanol; DL-7-azatryptophan; DL-4- and DL-6-flurotryptophan; 5-hydroxytryptamine; L-5-hydroxytryptophan; DL-α-methyltryptamine; α- and β-methyl-DL-tryptophan; tryptamine; DL-2-amino-1-(4-hydroxyphenyl)-1-propanol; DL-3-fluorotyrosine; 3-iodo-L-tyrosine; 3-nitro-L-tyrosine; L-tyrosinol.HCl; L-threo-2-amino-3-chlorobutyric acid; hexafluoro-DL-valine; DL-norvaline; L-4-thialysine; DL-ethionine; N,N'-di-CBZ-L-lysine; DL-3-fluorophenylalanine; DL-4-fluorophenylalanine; DL-3,4-dihydroxyphenylalanine; or mixtures thereof.

Further tRNA synthetase inhibitors for use in the compositions described herein include any tRNA synthetase inhibitor as known to those of skill in the art. For example, the tRNA synthetase inhibitor can be a tRNA synthetase inhibitor found in Lv and Zhu, Current Medicinal Chemistry, 19(21): 3550-3563 (2012); Teng et al., Journal of Medicinal Chemistry, 56: 1748-1760 (2013); Hurdle et al., Antimicrobial Agents and Chemotherapy, 49(12): 4821-4833 (2005); Orelle et al., Nucleic Acids Research, 41(14); e144 (2013); and Zhao et al., Int. J. Mol. Sci., 15: 1358-1373 (2014), which are incorporated herein by reference in their entireties, at least, for tRNA synthetases and tRNA synthetase inhibitors taught therein.

c. Synergistic Compositions

The compositions described herein are synergistic combinations of at least one RNAse P inhibitor as described herein and at least one tRNA synthetase inhibitor as described herein.

An exemplary synergistic composition includes mupirocin and an RNase P inhibitor of the following structure:

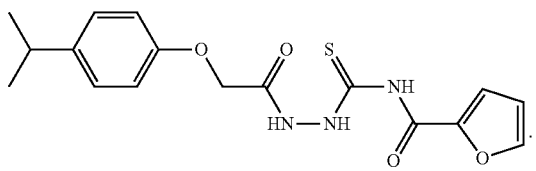

ST003531 (RNPA2000)

Optionally, the synergistic composition includes mupirocin in combination with one or more of the following structures:
ST5523108
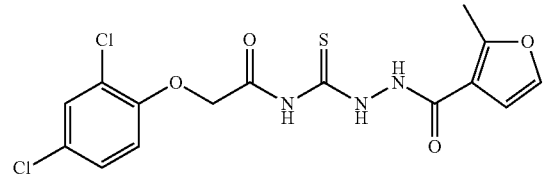
ST5523326
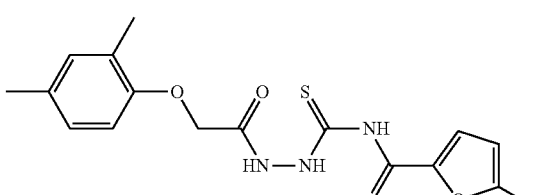
ST5523335
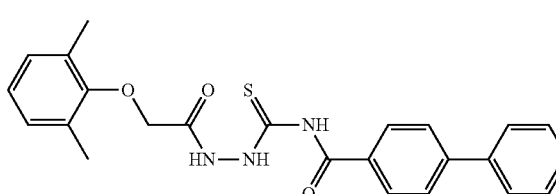
ST5524693
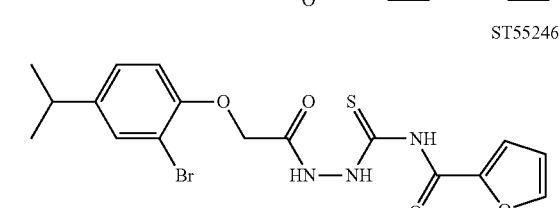
ST5528488
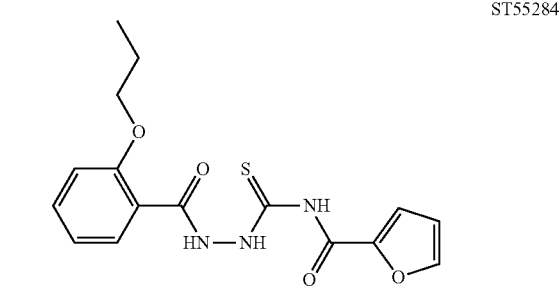
ST5682782
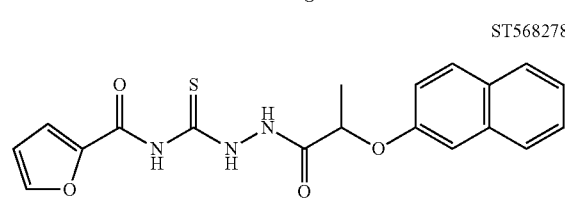
ST5682783
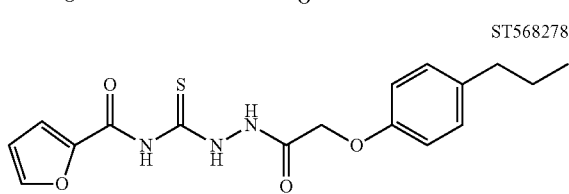
ST5684191
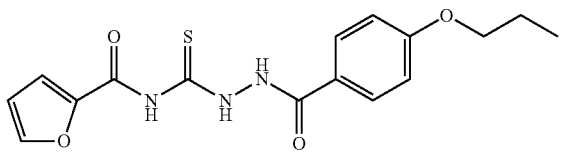
MC-190029
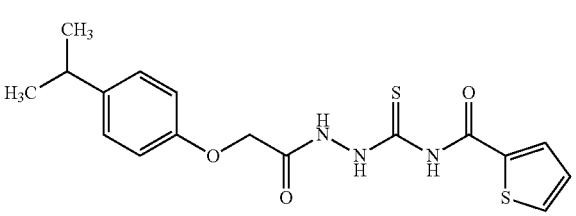
MC-190030
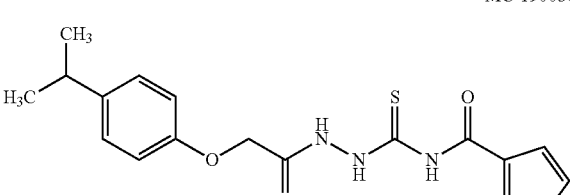
MC-190031
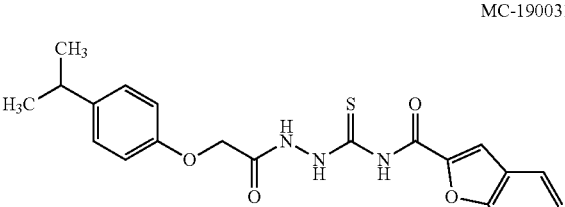
MC-190033
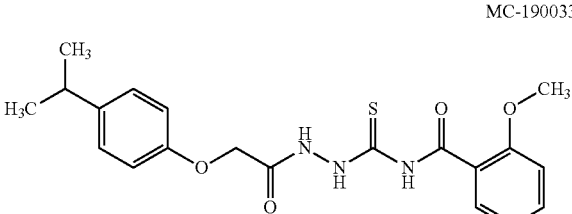
MC-190042
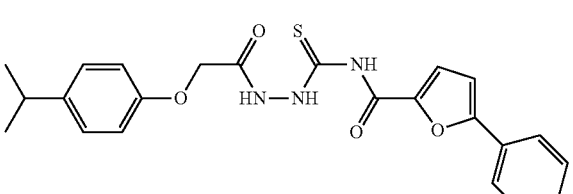
MC-190044
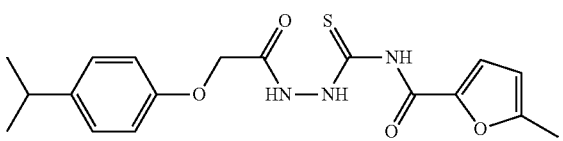

-continued

MC-190046

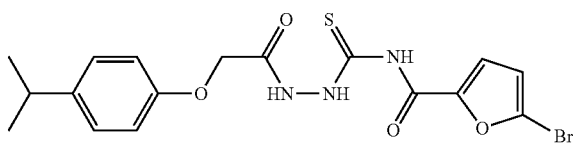

MC-190053

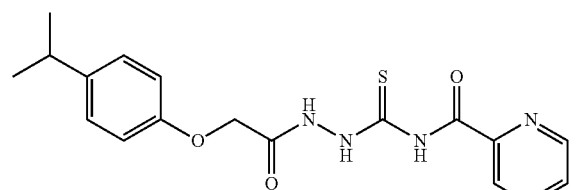

MC-190054

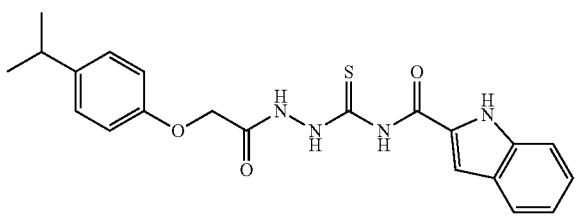

MC-190056

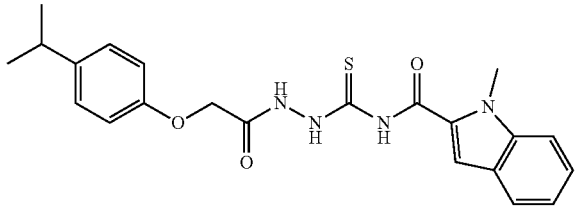

MC-190058

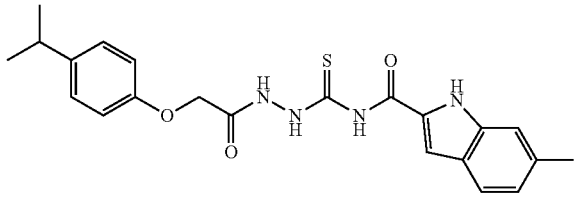

MC-190060

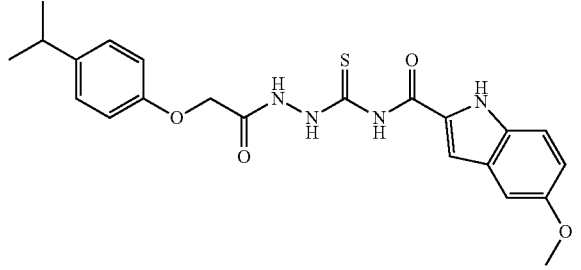

MC-190068

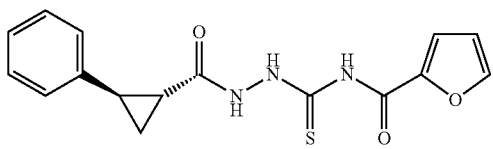

-continued

MC-190071

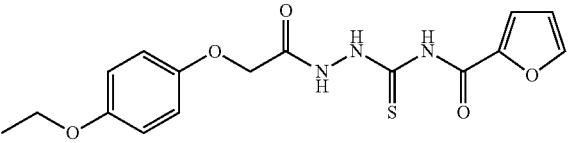

II. Pharmaceutical Formulations

The compounds described herein or derivatives thereof can be provided in a pharmaceutical composition. Depending on the intended mode of administration, the pharmaceutical composition can be in the form of solid, semi-solid or liquid dosage forms, such as, for example, ointments, gels, creams, tablets, suppositories, pills, capsules, powders, liquids, suspensions, or solutions, preferably in unit dosage form suitable for single administration of a precise dosage. The compositions will include a therapeutically effective amount of the compound described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 22d Edition, Loyd et al. eds., Pharmaceutical Press and Philadelphia College of Pharmacy at University of the Sciences (2012).

Examples of physiologically acceptable carriers include buffers, such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers, such as polyvinylpyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, N.J.), polyalkylene glycols, such as polyethylene glycol (PEG), and PLURONICS™ (BASF; Florham Park, N.J.). Optionally, the carrier is a polyalkylene glycol carrier. Optionally, the polyalkylene glycol carrier is a polyethylene glycol carrier.

Compositions containing one or more of the compound described herein or derivatives thereof suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants, such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier), such as sodium citrate or dicalcium phosphate, or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of one or more of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, may contain one or more additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the one or more compounds described herein or derivatives thereof for rectal administrations are optionally suppositories, which can be prepared by mixing the compounds with suitable non-irritating excipients or carriers, such as cocoa butter, polyethyleneglycol or a suppository wax, which are solid at ordinary temperatures but liquid at body temperature and, therefore, melt in the rectum or vaginal cavity and release the active component(s).

Dosage forms for topical administration of the one or more compounds described herein or derivatives thereof include ointments, powders, sprays, inhalants, gels, creams, and solutions. The compounds described herein or derivatives thereof are admixed under sterile conditions with a physiologically acceptable carrier and any preservatives, buffers, or propellants as may be required. Ophthalmic formulations, ointments, powders, and solutions are also contemplated as being within the scope of the compositions.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., *J. Pharm. Sci.* (1977) 66, 1, which is incorporated herein by reference in its entirety, at least, for compositions taught therein.)

Administration of the compounds and compositions described herein or pharmaceutically acceptable salts thereof can be carried out using therapeutically effective amounts of the compounds and compositions described herein or pharmaceutically acceptable salts thereof as described herein for periods of time effective to treat a disorder. The effective amount of the compounds and compositions described herein or pharmaceutically acceptable salts thereof as described herein may be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Those of skill in the art will understand that the specific dose level and frequency of dosage for any particular subject may be varied and will depend upon a variety of factors, including the activity of the specific compound or compounds employed, the metabolic stability and length of action of the compound(s); the species, age, body weight, general health, sex and diet of the subject; the mode and time of administration; rate of excretion; drug combination; and severity of the particular condition.

III. Methods of Making the Compounds

The compounds described herein can be prepared in a variety of ways known in the art of organic synthesis or variations thereon as appreciated by those skilled in the art. The compounds described herein can be prepared from readily available starting materials. Optimum reaction conditions may vary with the particular reactants or solvents used, but such conditions can be determined by one skilled in the art.

Variations on Formula I, Formula II, and the compounds described herein include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety. The synthesis and subsequent testing of various compounds as described herein to determine efficacy is contemplated.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Optionally, the compounds described herein can be obtained from commercial sources, including, for example, Teva Pharmaceuticals USA (North Wales, Pa.).

IV. Methods of Use

Provided herein are methods to treat, prevent, or ameliorate microbial infections in a subject. The methods include administering to the subject an effective amount of a combination of an RNase P inhibitor and a tRNA synthetase inhibitor as described herein. The RNaseP inhibitor and the tRNA synthetase inhibitor can be administered concomitantly or sequentially.

The compositions described herein are useful for treating microbial infections in humans, e.g., pediatric and geriatric populations, and in animals, e.g., veterinary applications. Microbial infections include, for example, bacterial infections and fungal infections. In some examples, the microbial infection is a bacterial infection. In some examples, the microbial infection is a Gram-positive bacterial infection, such as a *Staphylococcus* infection (e.g., a *Staphylococcus aureus* infection), a *Bacillus* infection, a *Listeria* infection, a *Streptococcus* infection (e.g., a *Streptococcus pyogenes* infection), an *Enterococcus* infection, or a *Clostridium* infection. Optionally, the bacterial infection is a Gram-negative bacterial infection, such as an *Acinetobacter* infection (e.g., an *Acinetobacter baumannii* infection), a *Pseudomonas* infection (e.g., a *Pseudomonas aeruginosa* infection), a *Klebsiella* infection, an *Escherichia* infection, a *Salmonella* infection, a *Yersinia* infection, a *Shigella* infection, a *Proteus* infection, an *Enterobacter* infection, a *Serratia* infection, or a *Citrobacter* infection.

Optionally, the bacterial infection is drug resistant bacterial infection. For example, the bacterial infection can be a drug-resistant *Staphylococcus aureus* infection, such as a mupirocin-resistant *Staphylococcus aureus* infection.

The methods of treating, preventing, or ameliorating microbial infections in a subject can further include selecting a subject infected with or at risk of being infected with a microbe that is resistant to the antimicrobial agent. Optionally, the methods of treating, preventing, or ameliorating microbial infections in a subject can further include selecting a subject infected with or at risk of being infected with a microbe that is capable of developing resistance to the antimicrobial agent. Subjects at risk of being infected with a microbe as described above include young children, the elderly, immuno-compromised subjects, hospitalized subjects, subjects living in institutions (e.g., nursing homes), subjects having an invasive medical device (e.g., a urinary catheter), subjects having open wounds, and subjects that have come into contact with others infected with the microbe.

These methods can further include treatment with one or more additional therapeutic agents (e.g., an antibiotic). The one or more additional agents and the compounds and compositions or pharmaceutically acceptable salts thereof as described herein can be administered in any order, including simultaneous administration, as well as sequentially (e.g., temporally spaced order of up to several days apart). The methods may also include more than a single administration of the one or more additional agents and/or the compounds and compositions or pharmaceutically acceptable salts thereof as described herein. The administration of the one or more additional agents and the compounds and compositions or pharmaceutically acceptable salts thereof as described herein may be by the same or different routes. When treating with one or more additional agents, the compounds and compositions or pharmaceutically acceptable salts thereof as described herein can be combined into a pharmaceutical composition that includes the one or more additional agents. For example, the compounds and compositions or pharmaceutically acceptable salts thereof as described herein can be combined into a pharmaceutical composition with an antibiotic. Suitable antibiotics can include any antibiotic effective for treating a bacterial infection and include, for example, tetracyclines (e.g., minocycline), quinolones (e.g., ciprofloxacin, levofloxacin, and nalidixic acid), aminoglycosides (e.g., amikacin, gentamycin, kanamycin, and tobramycin), carbapenems (e.g., meropenem), cephalosporins (e.g., ceftriaxone), macrolides (e.g., erythromycin), polypeptides (e.g., colistin and polymxin B), sulfonamides (e.g., sulfamethoxazole), glycylcyclines (e.g., tigecycline), beta lactams (e.g., penams), lipopeptides (e.g., daptomycin), oxazolidinones (e.g., linezolid), and trimethoprim.

The methods and compounds as described herein are useful for both prophylactic and therapeutic treatment. As used herein the term treating or treatment includes prevention; delay in onset; diminution, eradication, or delay in exacerbation of signs or symptoms after onset; and prevention of relapse. For prophylactic use, a therapeutically effective amount of the compounds and compositions or pharmaceutically acceptable salts thereof as described herein are administered to a subject prior to onset (e.g., before obvious signs of a microbial infection), during early onset (e.g., upon initial signs and symptoms of a microbial infection), after an established microbial infection, or even after resistance to antibiotic occurs. Prophylactic administration can occur for several days to years prior to the manifestation of symptoms of an infection. Therapeutic treatment involves administering to a subject a therapeutically effective amount of the compound(s) and composition(s) or pharmaceutically acceptable salts thereof as described herein after a microbial infection is diagnosed.

Also provided herein are methods of inhibiting a bacterial tRNA synthetase in a cell. The bacterial tRNA synthetase can be an aminoacyl tRNA synthetase, such as a prolyl tRNA synthetase, a cysteinyl tRNA synthetase, a methionyl tRNA synthetase, a leucyl tRNA synthetase, a tryptophanyl tRNA synthetase, a glycyl tRNA synthetase, an alanyl tRNA synthetase, a valyl tRNA synthetase, an isoleucyl tRNA synthetase, an aspartyl tRNA synthetase, a glutamyl tRNA synthetase, an asparagyl tRNA synthetase, a glutaminyl tRNA synthetase, a seryl tRNA synthetase, a threonyl tRNA synthetase, a lysyl tRNA synthetase, an arginyl tRNA synthetase, a histidyl tRNA synthetase, a phenylalanyl tRNA synthetase, a tyrosyl tRNA synthetase, or a glutamyl-prolyl-tRNA synthetase (EPRS).

The methods of inhibiting a bacterial tRNA synthetase in a cell can include contacting the cell with an effective amount of a composition as described herein. The effective amount of the composition can be the amount that inhibits a bacterial tRNA synthetase in the cell. Optionally, the cell can be a microbial cell. Optionally, the microbial cell can be a bacterial cell. Optionally, the bacterial cell is a gram-positive bacterial cell. Optionally, the gram-positive bacterial cell is a *Staphylococcus* bacterial cell (e.g., a *Staphylococcus aureus* bacterial cell), a *Bacillus* bacterial cell, a *Listeria* bacterial cell, a *Streptococcus* bacterial cell (e.g., a *Streptococcus pyogenes* bacterial cell), an *Enterococcus* bacterial cell, or a *Clostridium* bacterial cell. Optionally, the bacterial cell is a gram-negative bacterial cell. Optionally, the gram-negative bacterial cell is an *Acinetobacter* bacterial cell (e.g., an *Acinetobacter baumannii* bacterial cell), a *Pseudomonas* bacterial cell (e.g., a *Pseudomonas aeruginosa* bacterial cell), a *Klebsiella* bacterial cell, an *Escherichia* bacterial cell, a *Salmonella* bacterial cell, a *Yersinia* bacterial cell, a *Shigella* bacterial cell, a *Proteus* bacterial cell, an *Enterobacter* bacterial cell, a *Serratia* bacterial cell, or a *Citrobacter* bacterial cell. The contacting can be in vivo (e.g., in a human subject) or in vitro. Optionally, the cell can be a drug resistant cell, such as a mupirocin-resistant cell. Optionally, the mupirocin-resistant cell is a mupirocin-resistant *Staphylococcus aureus* cell.

Also provided herein are methods of decolonizing bacteria on a surface. The methods of decolonizing bacteria on a surface include contacting the surface with an effective amount of a composition as described herein. The effective amount of the composition can be the amount that decolonizes bacteria on a surface. Optionally, the surface is a human body surface, such as a mucosal surface. Optionally, the mucosal surface is a nasal cavity surface.

V. Kits

Also provided herein are kits for treating or preventing microbial infections (e.g., bacterial infections) in a subject. A kit can include any of the compositions described herein. Optionally, the kit can include one or more additional agents, such as an antibiotic agent. For example, a kit can include a composition as described herein and an antibiotic agent such as tetracyclines (e.g., minocycline), quinolones (e.g., ciprofloxacin, levofloxacin, and nalidixic acid), aminoglycosides (e.g., amikacin, gentamycin, kanamycin, and tobramycin), a carbapenem (e.g., meropenem), a cephalosporin (e.g., ceftriaxone), a macrolide (e.g., erythromycin), polypeptides (e.g., colistin and polymxin B), a sulfonamide (e.g., sulfamethoxazole), glycylcycline (e.g., tigecycline), and trimethoprim. A kit can further include an ointment formulation of any of the compounds or compositions described herein. A kit can additionally include directions for use of the kit (e.g., instructions for treating a subject), one or more containers (for the compound(s), composition(s), or additional agent(s)), a means for administering the compounds or compositions, and/or a carrier.

As used herein the terms treatment, treat, or treating refer to reducing one or more symptoms of an infection, a disease, or a condition. Thus in the disclosed method, treatment can refer to a reduction by 10%, 20%, 30%, 40%, 50%, 60%, 70%, 80%, 90%, 100%, or any percent reduction in between 10% and 100% in the severity of one or more symptoms of the infection, disease, or condition. For example, a method for treating an infection is considered to be a treatment if there is a 10% reduction in one or more symptoms or signs of the infection in a subject as compared to a control. As used herein, control refers to the untreated infection. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the infection, disease, condition, or symptoms of the infection, disease, or condition.

As used herein, the terms prevent, preventing, and prevention of an infection, disease, or disorder refer to an action, for example, administration of a composition or therapeutic agent, that occurs before or at about the same time a subject begins to show one or more symptoms of the disease or disorder, which inhibits or delays onset or severity of one or more symptoms of the disease or disorder.

As used herein, references to decreasing, reducing, or inhibiting include a change of 10%, 20%, 30%, 40%, 50%, 60%, 70%, 80%, 90% or greater, or any percent change in between 10% and greater than about 90% or greater, as compared to a control level. Such terms can include, but do not necessarily include, complete elimination.

As used herein, subject means both mammals and non-mammals. Mammals include, for example, humans; non-human primates, e.g., apes and monkeys; cattle; horses; sheep; rats; mice; pigs; and goats. Non-mammals include, for example, fish and birds.

The examples below are intended to further illustrate certain aspects of the methods and compositions described herein, and are not intended to limit the scope of the claims.

EXAMPLES

Example 1

RNPA2000 is an Antimicrobial Agent that Affects RnpA Mediated tRNA Processing.

Mupirocin is a generically available antibiotic that inhibits isoleucyl tRNA synthetase in bacterial cells. The enzyme charges tRNA molecules, allowing them to participate in protein translation. RnpA is an enzyme, which together with the ribozyme, rnpB, forms RNase P riboprotein complex that prepares precursor tRNA molecules for charging (it works upstream of tRNA synthetase in the tRNA processing pathway). RNPA2000 inhibits precursor tRNA processing in vitro (FIG. 1, Panel A) and also within bacterial cells (FIG. 1, Panel B).

RNPA2000 Works Synergistically with Mupirocin in Laboratory Medium.

RNPA2000 affects an enzyme upstream of tRNA isoleucyl tRNA synthetase and acts synergistically with mupirocin in laboratory medium. Fractional Inhibitory Concentration (FIC) measures revealed a synergistic effect with RNPA2000 (FIC=0.44) when combined with mupirocin.

RNPA2000 Works Synergistically with Mupirocin in Mupirocin Ointment.

Figure 2:
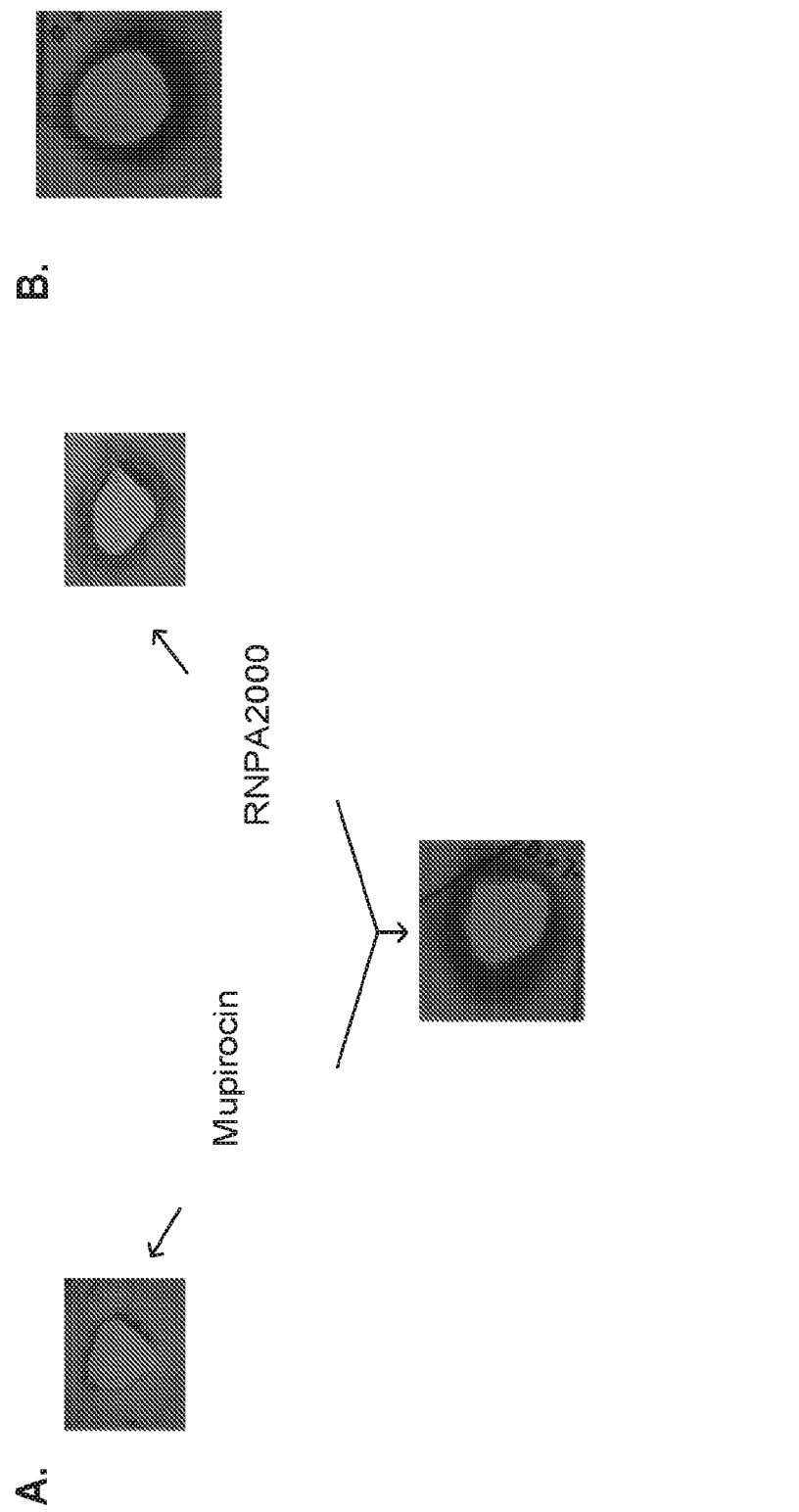
FIG. 2 contains photographs demonstrating the antimicrobial activity of mupirocin ointment suspended in petroleum jelly (Panel A, left corner), RNPA2000 suspended in petroleum jelly (Panel A, right corner), and mupirocin ointment and RNPA2000 suspended in petroleum jelly (Panel A, lower picture) against *Staphylococcus aureus*. Panel B shows the antimicrobial activity of mupirocin and RNPA2000 suspended in petroleum jelly against mupirocin-resistant *Staphylococcus aureus*.

The addition of an RnpA inhibitor, such as RNPA2000, to mupirocin ointment (Teva Pharmaceuticals USA (North Wales, Pa.)) improved the antimicrobial efficacy of the ointment and is also effective against mupirocin resistant *S. aureus*. As shown in FIG. 2, dilution of mupirocin ointment with petroleum jelly reduces the antimicrobial properties of the ointment. See FIG. 2, Panel A, upper left picture. Likewise, extremely low levels of RNPA2000 in petroleum jelly display no antimicrobial properties. See FIG. 2, Panel A, upper right picture. However, when these two (both at subinhibitory concentration) are mixed, clear antibacterial effects are seen (FIG. 2, Panel A, lower picture), establishing that RNPA2000 and mupirocin act synergistically in commercially available mupirocin ointment. RNPA2000 and mupirocin also act synergistically against mupirocin-resistant *S. aureus* (FIG. 2, Panel B).

Example 2: Antimicrobial Susceptibility Testing

The RNase P inhibitors described herein were tested for antimicrobial activity toward *Staphylococcus aureus* strain UAMS-1. Individual wells of a 96-well microtiter plate were inoculated with ~1×10$^5$ colony-forming units (CFU) of the indicated organism, containing two-fold increasing concentrations (from 0 to 256 µg mL$^{-1}$) of the indicated antibiotic or putative RnpA inhibitor, and incubated at 37° C. for 18 hours in Mueller Hinton broth. The MIC was defined as the lowest concentration of antibiotic in which there was no visible bacterial growth in the wells. Minimum bactericidal concentration testing was performed by enumerating the bacterial cells in each of the wells containing treatments at and above the MIC. The concentration of the test agent that resulted in 99.9% cell death of the starting inoculum was determined to be the minimum bactericidal concentration. The MIC results are shown in Table 1.

Example 3: RNA Degradation Activity

The RNase P inhibitors described herein were tested for activity toward RnpA mRNA degradation activity. Either 1 µg of total *S. aureus* RNA or 1 pmol of in vitro synthesized spa mRNA was incubated with 20 pmol RnpA at 37° C. for 15 to 30 min in a reaction buffer (50 mM Tris-HCl pH 8.0, 2 mM NaCl, 2 mM MgCl$_2$) in the absence or presence of the indicated compound. Reactions were stopped by adding an equal volume of 2×RNA loading dye (95% formamide, 0.025% SDS, 0.025% bromophenol blue, 0.025% xylene cyanol FF, 0.5 mM EDTA), run on a denaturing 1.0% agarose-0.66 M formaldehyde gel and stained with ethidium bromide. RNA substrates and corresponding degradation products were visualized using a FluorChem 5500 system (Alpha Innotech; San Leandro, Calif.). The inhibitory effects of the test compounds were measured using Image J densitometry software (National Institutes of Health; Bethesda, Md.) to quantify the signal intensity of the RNA band(s) in the negative control (RNA alone), positive control (RnpA+RNA+DMSO), and experimental samples (RnpA+RNA+test compound). The percent enzyme inhibition of test compounds was calculated using the following equation: Percent inhibition=[(experimental signal-positive control)/(negative control signal-positive control signal)]*100. The RnpA mRNA degradation results are shown in Table 1.

Example 4: RNase P Activity

The RNase P inhibitors described herein were tested for activity toward RNase P. *S. aureus* RNase P activity assays were performed in low salt buffer (50 mM Tris-HCl pH 8.0, 5 mM MgCl$_2$) or in high salt buffer (50 mM Tris-HCl pH 8.0, 100 mM MgCl$_2$, 800 mM NH$_4$Cl). For all reactions, ptRNATyr, tRNATyr, or rnpB RNA species were first denatured by heating to 95° C. for 3 minutes, and then slowly cooling the mixtures to room temperature. RNase P was reconstituted by mixing an equal molar ratio of RnpB and RnpA for 15 min at 37° C. Precursor tRNA processing reactions (20 µL) were performed by mixing 1.25 pmol RNase P (RnpA+rnpB), RnpA, or rnpB with an equal volume of 2× low salt buffer or 2× high salt buffer and 10 pmol ptRNATyr. Mixtures were incubated for 15 min at 37° C. Reactions were stopped by adding 20 µL 2×RNA loading dye (95% formamide, 0.025% SDS, 0.025% bromophenol blue, 0.025% xylene cyanol FF, 0.5 mM EDTA), and 30 µL of each sample was electrophoresed in a 7 M urea/8% polyacrylamide gel and was then stained with ethidium bromide (0.5 µg/ml). Where indicated, reactions were repeated in the presence of the indicated amount of putative RnpA inhibitors or dimethyl sulfoxide (DMSO). A FluorChem 5500 imaging system was used to visualize the RNA, and the relative abundance of the mature tRNATyr band in the positive control (RNase P+DMSO) or in samples containing test compounds was measured using Image J densitometry software (NIH). The percent RNase P activity was then calculated using the following calculation: (test compound tRNATyr signal/positive control tRNATyr signal) *100. The RNase P activity results are shown in Table 1.

Example 5: Fractional Inhibitory Concentration

The RNase P inhibitors described herein were tested for Fractional Inhibitory Concentration (FIC) in the presence of mupirocin. FIC testing was performed to determine the combined effects of mupirocin and the RnpA inhibitors as described herein. Individual wells of a 96-well microtiter plate were inoculated with $1\times10^5$ CFU of *S. aureus* strain UAMS-1 in a Mueller Hinton broth. Each row of the plate contained increasing concentrations of RNPA1000 or RNPA2000 (two-fold increments; 0, 0.004, 0.008, 0.016, 0.03, 0.06, 0.125, 0.25, 0.5, 1, 2, or 4×MIC), whereas each column contained increasing concentrations of the indicated antibiotic (two-fold increments; 0, 0.06, 0.125, 0.25, 0.5, 1, 2, or 4×MIC). Plates were incubated for 18 hours at 37° C., and growth was detected by the unaided eye. The FIC was determined using the following formula: (MIC of Drug A in Combination/MIC of Drug A Alone)+(MIC of Drug B in Combination/MIC of Drug B Alone)=FIC. A synergistic interaction was defined as an FIC value≤0.5, no interaction as an FIC of 0.5-4, or an antagonistic interaction FIC>4. The FIC results are shown in Table 1.

TABLE 1

| ID | MIC (µg/ml) | RnpA $IC_{50}$ (µM) | RNase P $IC_{50}$ (µM) | FIC with Mupirocin |
|---|---|---|---|---|
| RNPA2000 (ST003531) | 16 | 275 | 140 | 0.44 |
| ST4145527 | >128 | >500 | >500 | — |
| ST5254069 | 16 | >500 | >500 | — |
| ST5254078 | 128 | >500 | >500 | — |
| ST5254083 | 16 | 90 | 75 | — |
| ST5254088 | >128 | 500 | >500 | — |
| ST5254089 | 64 | >500 | 180 | — |
| ST5521633 | 16 | 500 | 155 | — |
| ST5521953 | 32 | >500 | >500 | — |
| ST5522690 | 16 | >500 | >500 | 1 |
| ST5522821 | 16 | 35 | 220 | 0.75 |
| ST5523108 | 4 | >500 | 75 | 0.49 |
| ST5523210 | 32 | 45 | 110 | 0.75 |
| ST5523216 | 32 | >500 | 425 | — |
| ST5523314 | 8 | >500 | >500 | 1 |
| ST5523326 | 8 | 380 | 75 | 0.375 |
| ST5523335 | 128 | >500 | 100 | 0.375 |
| ST5523339 | 16 | >500 | 50 | 1 |
| ST5524187 | 32 | 175 | 65 | — |
| ST5524465 | 32 | 45 | 65 | 0.625 |
| ST5524510 | >128 | 500 | >500 | — |
| ST5524527 | 8 | >500 | 200 | 0.625 |
| ST5524693 | 8 | 500 | 350 | 0.49 |
| ST5524973 | 32 | 220 | 80 | — |
| ST5524997 | 32 | 300 | 70 | — |
| ST5525281 | — | 275 | 125 | — |
| ST5525289 | 64 | 40 | >500 | — |
| ST5525332 | 8 | >500 | >500 | — |
| ST5525955 | >128 | >500 | 145 | — |
| ST5525958 | 32 | >500 | 125 | 0.75 |
| ST5526667 | >128 | 80 | 90 | — |
| ST5526682 | >128 | >500 | 200 | — |
| ST5528171 | 64 | >500 | 280 | — |
| ST5528173 | 32 | >500 | 230 | 1 |
| ST5528488 | 4 | 430 | 95 | 0.5 |
| ST5528839 | >128 | 500 | >500 | — |
| ST5528863 | >128 | >500 | 490 | — |
| ST5528880 | >128 | >500 | 380 | 0.56 |
| ST5528960 | >128 | 40 | >500 | 0.56 |
| ST5529685 | 64 | >500 | >500 | — |
| ST5607017 | >128 | 70 | >500 | — |
| ST5607269 | >128 | 150 | >500 | — |
| ST5607293 | >128 | >500 | >500 | — |
| ST5638647 | 128 | >500 | >500 | — |
| ST5638707 | 128 | >500 | >500 | — |
| ST5638722 | 64 | >500 | 430 | — |
| ST5640720 | 16 | >500 | >500 | — |
| ST5641784 | 32 | >500 | >500 | — |
| ST5642600 | 16 | >500 | >500 | — |
| ST5682126 | >128 | 500 | >500 | — |
| ST5682777 | 16 | >500 | 70 | — |
| ST5682778 | >128 | >500 | >500 | — |
| ST5682782 | >128 | >500 | >500 | 0.25 |
| ST5682783 | >128 | >500 | 65 | 0.31 |
| ST5682846 | 4 | >500 | 80 | — |
| ST5684191 | 8 | >500 | >500 | 0.375 |
| ST5703018 | 64 | >500 | >500 | 0.625 |
| ST5703881 | 16 | >500 | >500 | — |
| ST5704832 | >128 | >500 | >500 | — |
| MC-190029 | 128 | >500 | 380 | 0.5 |
| MC-190030 | 64 | >500 | 395 | 0.375 |
| MC-190031 | 32 | 60 | 1 | 0.25 |
| MC-190032 | >128 | >500 | 75 | 0.75 |
| MC-190033 | 128 | 250 | >500 | 0.3125 |
| MC-190034 | >256 | >500 | >500 | — |
| MC-190035 | >256 | >500 | >500 | — |
| MC-190036 | >256 | >500 | >500 | — |
| MC-190037 | 32 | >500 | >500 | 0.625 |
| MC-190038 | >256 | >500 | >500 | — |
| MC-220000 (RNPA2000) | 8 | 180 | 300 | 0.44 |
| MC-220001 | >256 | 50 | 100 | 0.56 |
| MC-190039 | 64 | >500 | 50 | — |
| MC-190040 | >256 | 480 | 230 | 0.625 |
| MC-190041 | >256 | 470 | 385 | — |
| MC-190042 | 64 | 40 | 50 | 0.45 |
| MC-190043 | 32 | 20 | 150 | — |
| MC-190044 | 32 | 30 | 105 | 0.49 |
| MC-190045 | 64 | 100 | 32 | 0.625 |
| MC-190046 | 32 | 30 | 140 | 0.3125 |
| MC-190047 | 64 | 30 | 26 | 0.625 |
| MC-190048 | >256 | <50 | <50 | 0.5625 |
| MC-190049 | 64 | >500 | 160 | 1 |
| MC-190050 | 128 | >500 | 150 | — |
| MC-190051 | 128 | 45 | 2 | — |
| MC-190052 | 128 | 150 | 90 | 0.56 |
| MC-190053 | 32 | 100 | 1 | 0.49 |
| MC-190054 | 16 | 50 | <0.5 | 0.49 |
| MC-190055 | 32 | 40 | 90 | 0.56 |
| MC-190056 | 64 | 240 | 50 | 0.49 |
| MC-190057 | >256 | >500 | 70 | — |
| MC-190058 | 64 | 50 | 50 | 0.49 |
| MC-190059 | >256 | 150 | 80 | — |
| MC-190060 | 32 | 50 | <50 | 0.49 |
| MC-190062 | 64 | <50 | <50 | 0.56 |
| MC-190064 | 256 | >500 | 100 | 0.53 |
| MC-190066 | 16 | 250 | <50 | 0.75 |
| MC-190067 | 8 to 16 | >500 | >500 | 0.625 |
| MC-190068 | 32 | >500 | 370 | 0.5 |
| MC-190069 | 64 | >500 | 470 | — |
| MC-190070 | 64 | >500 | >500 | — |
| MC-190071 | 256 | >500 | >500 | 0.375 |
| MC-190072 | 128 | — | — | 0.625 |
| MC-190073 | 64 | — | — | 0.75 |
| MC-190074 | 64 | — | — | 0.625 |
| MC-190077 | >128 | — | — | 0.53 |
| MC-190078 | 64 | — | — | 0.625 |
| MC-190079 | >128 | — | — | 0.75 |
| MC-190080 | >128 | — | — | — |
| MC-190081 | >128 | — | — | 0.56 |
| MC-190082 | >128 | — | — | — |
| MC-190083 | >128 | — | — | — |
| MC-190084 | 16 | — | — | — |
| MC-190085 | >128 | — | — | — |
| MC-190086 | >128 | — | — | — |
| MC-190087 | >128 | — | — | — |
| MC-190088 | >128 | — | — | — |
| MC-190090 | 256 | 50 | 50 | — |
| MC-190091 | 128 | 25 | 50 | — |
| MC-190092 | 256 | 250 | 250 | — |
| MC-190098 | 16 | — | 150 | — |

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods and combinations of various features of the compounds and methods are intended to fall within the scope of the appended claims, even if not specifically recited. Thus, a combination of steps, elements, components, or constituents may be explicitly mentioned herein; however, all other combinations of steps, elements, components, and constituents are included, even though not explicitly stated. All publications, patents, and patent applications cited herein are hereby incorporated by reference in their entireties for all purposes.

What is claimed is:

1. A topical composition comprising:
a compound (RNPA2000) of the following structure:

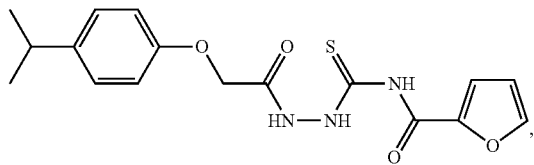 [SMILES: CC(C)c1ccc(OCC(=O)NNC(=S)NC(=O)c2ccco2)cc1]

mupirocin, and
a pharmaceutically acceptable carrier suitable for topical administration,
wherein a weight ratio of the RNPA2000 and the mupirocin is from about 100:1 to about 1000:1.

2. The topical composition of claim 1, wherein the weight ratio is from about 100:1 to about 400:1.

3. The topical composition of claim 1, wherein the topical composition comprises an ointment, a gel, a cream, a powder, a spray, a liquid, a suspension, or a solution.

4. The topical composition of claim 3, wherein the topical composition comprises an ointment.

5. A method of treating or preventing a microbial infection in a subject comprising administering to the subject an effective amount of a composition according to claim 1.

6. The method of claim 5, wherein the microbial infection is a bacterial infection.

7. The method of claim 6, wherein the bacterial infection is a gram-positive bacterial infection or a gram-negative bacterial infection.

8. The method of claim 6, wherein the bacterial infection is a *Staphylococcus* infection.

9. The method of claim 8, wherein the *Staphylococcus* infection is a *Staphylococcus aureus* infection or a *Staphylococcus pyogenes* infection.

10. A method of decolonizing bacteria on a surface comprising contacting the surface with an effective amount of a composition comprising
a compound (RNPA2000) of the following structure:

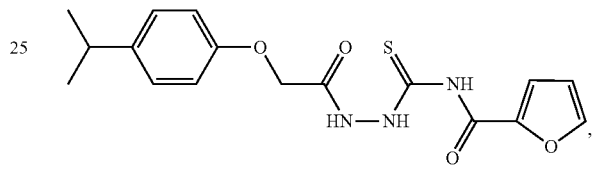

and
mupirocin,
wherein a weight ratio of the RNPA2000 and the mupirocin is from about 100:1 to about 1000:1.

* * * * *